(12) United States Patent
Calixto et al.

(10) Patent No.: US 11,135,430 B2
(45) Date of Patent: Oct. 5, 2021

(54) APPARATUSES AND METHODS FOR SETTING COCHLEAR IMPLANT SYSTEM STIMULATION PARAMETERS BASED ON ELECTRODE IMPEDANCE MEASUREMENTS

(71) Applicant: Advanced Bionics AG, Staefa (CH)

(72) Inventors: Roger Calixto, Valencia, CA (US); Kanthaiah Koka, Valencia, CA (US); Anthony J. Spahr, Newhall, CA (US); Mary Elizabeth Bush, Valencia, CA (US); Mark B. Downing, Valencia, CA (US); Leonid M. Litvak, Los Angeles, CA (US); Amy Stein, Sherman Oaks, CA (US)

(73) Assignee: Advanced Bionics AG, Staefa (CH)

( * ) Notice: Subject to any disclaimer, the term of this patent is extended or adjusted under 35 U.S.C. 154(b) by 99 days.

(21) Appl. No.: 16/487,827

(22) PCT Filed: Feb. 22, 2018

(86) PCT No.: PCT/US2018/019299
§ 371 (c)(1),
(2) Date: Aug. 21, 2019

(87) PCT Pub. No.: WO2018/156820
PCT Pub. Date: Aug. 30, 2018

(65) Prior Publication Data
US 2020/0054877 A1    Feb. 20, 2020

Related U.S. Application Data

(60) Provisional application No. 62/462,831, filed on Feb. 23, 2017.

(51) Int. Cl.
*A61N 1/00* (2006.01)
*A61N 1/36* (2006.01)
*A61N 1/05* (2006.01)

(52) U.S. Cl.
CPC ....... *A61N 1/36139* (2013.01); *A61N 1/0541* (2013.01); *A61N 1/3614* (2017.08);
(Continued)

(58) Field of Classification Search
CPC ............ A61N 1/36139; A61N 1/36038; A61N 1/3614; A61N 1/0541; A61N 1/36132; A61N 1/36157; A61N 1/36175
See application file for complete search history.

(56) References Cited

U.S. PATENT DOCUMENTS

| 7,107,101 B1 | 9/2006 | Faltys |
| 8,190,268 B2 | 5/2012 | Botros et al. |

(Continued)

FOREIGN PATENT DOCUMENTS

| CA | 1212501 | 10/1986 |
| EP | 0959943 | 12/1999 |

(Continued)

OTHER PUBLICATIONS

International Search Report and Written Opinion received in International Application No. PCT/US18/019299, dated Jul. 19, 2018.

(Continued)

*Primary Examiner* — Scott M. Getzow
(74) *Attorney, Agent, or Firm* — ALG Intellectual Property, LLC

(57) ABSTRACT

An apparatus associated with a cochlear implant system used by a patient directs a cochlear implant included within the cochlear implant system and implanted within the patient to generate electrical stimulation current at a predetermined current level. The apparatus further directs the cochlear (Continued)

implant to apply the electrical stimulation current to the patient by way of an electrode coupled with the cochlear implant, and to measure a voltage level associated with the electrode while the electrical stimulation current is applied to the patient by way of the electrode. Based on the predetermined current level and the measured voltage level, the apparatus determines an impedance of the electrode. Based on the determined electrode impedance and in accordance with a predetermined stimulation parameter adjustment constraint, the apparatus automatically adjusts a stimulation parameter associated with the cochlear implant system. Additional apparatuses and corresponding methods are also disclosed.

20 Claims, 12 Drawing Sheets

(52) U.S. Cl.
CPC ..... *A61N 1/36038* (2017.08); *A61N 1/36132* (2013.01); *A61N 1/36157* (2013.01); *A61N 1/36175* (2013.01)

(56) References Cited

U.S. PATENT DOCUMENTS

| | | | |
|---|---|---|---|
| 8,417,348 B2 | 4/2013 | Schleich | |
| 8,527,058 B2 | 9/2013 | Kulkarni et al. | |
| 8,751,006 B2 | 6/2014 | Saoji et al. | |
| 9,173,585 B2 | 11/2015 | Tsampazis et al. | |
| 9,179,231 B2 | 11/2015 | Johnston et al. | |
| 9,205,263 B2 | 12/2015 | King et al. | |
| 9,364,679 B2 | 6/2016 | John | |
| 9,409,017 B2 | 8/2016 | Tsampazis et al. | |
| 9,662,493 B2 | 5/2017 | Kals et al. | |
| 2011/0160799 A1 | 6/2011 | Mishra et al. | |
| 2011/0218593 A1* | 9/2011 | Rubinstein | A61N 1/36038 607/57 |
| 2012/0303096 A1* | 11/2012 | Kulkarni | A61N 1/36039 607/57 |
| 2013/0138180 A1 | 5/2013 | Kals et al. | |
| 2013/0282077 A1 | 10/2013 | Saoji et al. | |
| 2014/0126731 A1 | 5/2014 | Litvak et al. | |
| 2014/0303691 A1 | 10/2014 | McDermott | |
| 2015/0246230 A1 | 9/2015 | Litvak | |
| 2015/0265838 A1 | 9/2015 | Kals et al. | |
| 2015/0297891 A1 | 10/2015 | Litvak | |
| 2018/0161154 A1* | 6/2018 | Polak | A61N 1/0541 |

FOREIGN PATENT DOCUMENTS

| | | |
|---|---|---|
| EP | 2670479 | 12/2013 |
| WO | 97/48447 | 12/1997 |
| WO | 2009026625 | 3/2009 |
| WO | 2012106207 | 8/2012 |
| WO | 2012166108 | 12/2012 |
| WO | 2015053769 | 4/2015 |
| WO | 2015065401 | 5/2015 |
| WO | 2015126432 | 8/2015 |
| WO | 2015199934 | 12/2015 |
| WO | 2016024978 | 2/2016 |

OTHER PUBLICATIONS

Partial International Search Report received in International Application No. PCT/US18/019299, dated May 23, 2018.

* cited by examiner

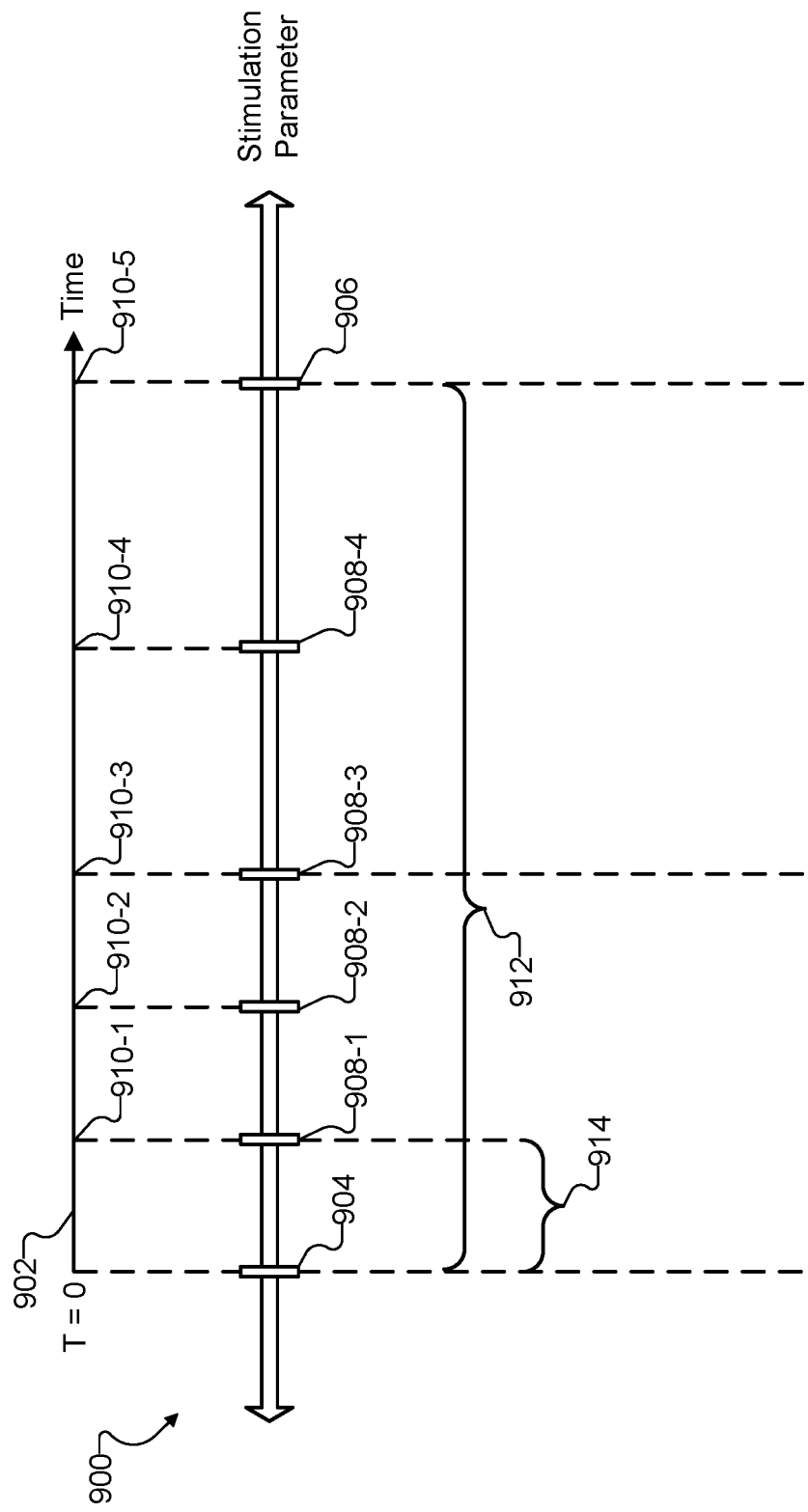

APPARATUSES AND METHODS FOR SETTING COCHLEAR IMPLANT SYSTEM STIMULATION PARAMETERS BASED ON ELECTRODE IMPEDANCE MEASUREMENTS

RELATED APPLICATIONS

The present application claims priority to U.S. Provisional Patent Application No. 62/462,831, filed Feb. 23, 2017. The contents of the provisional patent application are hereby incorporated by reference in their entirety.

BACKGROUND INFORMATION

The natural sense of hearing in human beings involves the use of hair cells in the cochlea that convert or transduce acoustic signals into auditory nerve impulses. Some types of hearing loss (e.g., sensorineural hearing loss) may occur when hair cells in the cochlea are absent or damaged, such that auditory nerve impulses cannot be generated from acoustic signals in the natural way. To overcome these types of hearing loss, cochlear implant systems have been developed. Cochlear implant systems bypass the hair cells in the cochlea by presenting electrical stimulation directly to the auditory nerve fibers by way of an array of electrodes implanted within the cochlea. Direct stimulation of the auditory nerve fibers leads to the perception of sound in the brain and at least partial restoration of hearing function.

Each electrode implanted within the cochlea may have a certain impedance associated therewith. For example, the impedance of an electrode may represent a measure of how difficult or easy it is to apply stimulation current to the patient by way of the electrode (e.g., a degree to which stimulation current flows into the patient by way of the electrode given a particular stimulation voltage level). The impedance of the electrodes in the array of electrodes implanted within the cochlea may be determined during an initial fitting session of a cochlear implant system to a patient (e.g., within a clinical setting) and may be used to determine one or more stimulation parameters during such a fitting session. Subsequent to the fitting session, however (e.g., after the patient has returned home and is no longer in the clinical setting), the impedance of one or more of the electrodes in the electrode array may change for a variety of reasons. Such changes, if unaccounted for, may result in decreased sound quality (e.g., distorted pitch, etc.) and/or loudness perceived by the patient, system malfunction of the cochlear implant system, and/or other undesirable outcomes.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 9 illustrates an exemplary predetermined adjustment timeline for setting cochlear implant system stimulation parameters based on electrode impedance measurements according to principles described herein.

DETAILED DESCRIPTION

Figure 1:
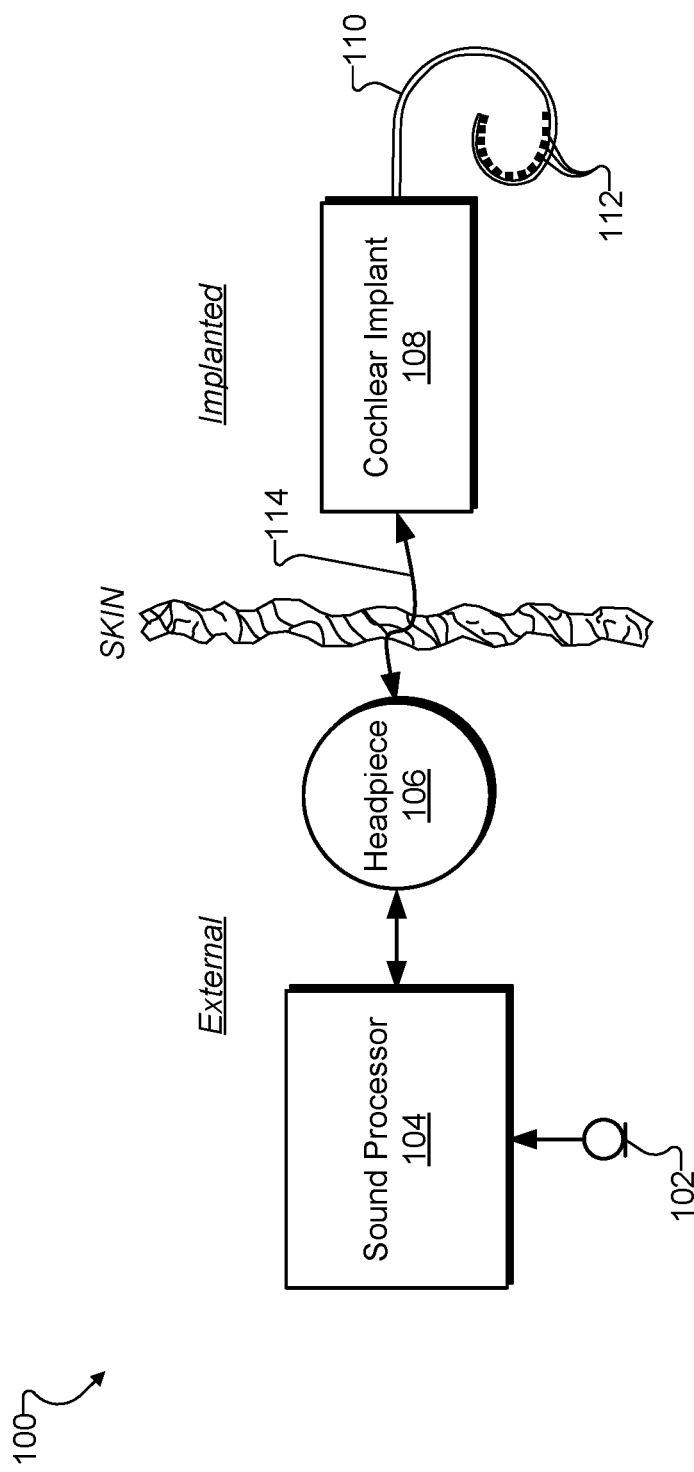
FIG. 1 illustrates an exemplary cochlear implant system according to principles described herein.

Apparatuses and methods for acquiring and using cochlear implant electrode impedance measurements are described herein. For example, as will be described in more detail below, the apparatuses and methods described herein may cause an electrode impedance of an electrode included within a cochlear implant system to be determined (e.g., detected, measured, etc.), and may perform one or more operations in response to the determination of the electrode impedance and/or based on the determined electrode impedance.

While various operations for using cochlear implant electrode impedance measurements after such measurements have been acquired are described herein, one exemplary area of focus of the present disclosure is related to apparatuses and methods for setting cochlear implant system stimulation parameters based on electrode impedance measurements. For instance, an exemplary apparatus according to principles described herein may be associated with a cochlear implant system used by a patient and may comprise at least one physical computing component that performs one or more of the following operations in the following order or in another suitable order as may serve a particular implementation. First, the apparatus may direct a cochlear implant (e.g., a cochlear implant included within the cochlear implant system and implanted within the patient) to generate electrical stimulation current at a predetermined current level and to apply the electrical stimulation current to the patient by way of an electrode coupled with the cochlear implant. Second, the apparatus may direct the cochlear implant to measure a voltage level associated with the electrode while the electrical stimulation current is applied to the patient by way of the electrode. Third, the apparatus may determine (e.g., based on the predetermined current level and the measured voltage level) an impedance of the electrode. Fourth, the apparatus may identify a predetermined stimulation parameter adjustment constraint. Fifth, the apparatus may automatically adjust (e.g., based on the impedance of the electrode and in accordance the predetermined stimulation parameter adjustment constraint) a stimulation parameter associated with the cochlear implant system.

Apparatuses for acquiring and using cochlear implant electrode impedance measurements (e.g., including apparatuses such as the exemplary apparatus described above for setting cochlear implant system stimulation parameters based on electrode impedance measurements) may be associated with a cochlear implant system used by a patient in any suitable way. For example, an apparatus may be included within the cochlear implant system as a component of the cochlear implant system (e.g., a sound processor of the cochlear implant system, a cochlear implant of the cochlear implant system, etc.). As another example, an apparatus may be separate from the cochlear implant system and associated with the cochlear implant system such as by being communicatively coupled with the cochlear implant system. For instance, the apparatus may be implemented by or within a mobile computing device (e.g., a smartphone, a tablet computing device, etc.) operated by the patient, a caregiver of the patient, or the like.

One exemplary implementation of an apparatus for setting cochlear implant system stimulation parameters based on electrode impedance measurements may be implemented by a cochlear implant implanted within a patient and included within a cochlear implant system. The cochlear implant may include a stimulation current generator configured to generate electrical stimulation current to be applied to the patient by way of an electrode on an electrode lead coupled to the cochlear implant. The cochlear implant may further include a voltage detector configured to measure a voltage level associated with the electrode. Additionally, the cochlear implant may include at least one physical computing component that, in a similar manner as described above, may be configured to: 1) direct the stimulation current generator to generate electrical stimulation current at a predetermined current level and to apply the electrical stimulation current to the patient by way of the electrode; 2) direct the voltage detector to measure the voltage level associated with the electrode while the electrical stimulation current is applied to the patient by way of the electrode; 3) determine (e.g., based on the predetermined current level and the measured voltage level) an impedance of the electrode; 4) identify a predetermined stimulation parameter adjustment constraint; and 5) automatically adjust (e.g., based on the impedance of the electrode and in accordance the predetermined stimulation parameter adjustment constraint) a stimulation parameter associated with the cochlear implant system.

As will be described in more detail below, cochlear implant systems may be configured to apply electrical stimulation to patients to directly stimulate auditory nerve fibers to at least partially restore the patient's hearing. To this end, a clinician or other professional overseeing the care of the patient with respect to the cochlear implant system may configure the cochlear implant system to apply stimulation in accordance with particular parameters specific to the patient's needs and preferences.

One parameter that a clinician may account for is an amount of charge that is applied by each electrode on every stimulation phase. Each of a plurality of electrodes on an electrode lead may be used to apply current to different stimulation sites within the patient's cochlea in a relatively fast sequence (e.g., a sequence that may occur at a stimulation rate or "pulse rate" that includes many stimulation pulses per second) such that the patient perceives stimulation occurring simultaneously in each of the different stimulation sites. According to Ohm's law, the relationship between the stimulation voltage ("V") generated by a voltage source, the stimulation current ("I") applied to the electrode, and the electrode impedance ("Z") may be defined as $V=I \times Z$. Accordingly, one technique for determining the electrode impedance of a given electrode may be by dividing (e.g., using at least one physical computing component such as a processor) a measured voltage level ("V") (e.g., a voltage level detected while a known stimulation current is being applied to the patient) by a predetermined current level ("I") that is known to be applied to the patient.

The charge applied by a particular electrode on a particular stimulation phase may be equal to an amount of current applied by the electrode multiplied by an amount of time that the current is applied by the electrode. This amount of time may commonly be referred to as a "pulse width," or, more precisely, as a "phase duration" of the applied current.

A particular patient may have unique charge requirements from other patients (e.g., as determined by a clinician) and, in certain cases, may even have unique charge requirements for each electrode implanted within the particular patient. For example, a typical average charge requirement that may suit a particular patient may be 20 nanocoulombs (nC) of charge, while a typical range for comfortable loudness for the particular patient may be 5 nC (which may barely be perceptible to the patient) up to 60 nC (which may be as loud a sound as the patient is comfortable hearing).

Because charge incorporates both a stimulation current level and a pulse width time, a particular charge targeted for a particular patient presented with a sound having a particular loudness (e.g., a relatively high charge representative of a relatively loud sound) may be applied by way of various combinations of stimulation current level and pulse width time. For example, to avoid having to apply a stimulation current level that is too high (e.g., higher than a current source of the cochlear implant is configured to provide), a particular charge may be achieved by applying stimulation at a lower stimulation current level for a longer pulse width time. Similarly, to avoid having to apply a pulse width for too long (e.g., such that a stimulation rate associated with the pulse width time would be too low, causing sound quality to deteriorate), a particular charge may be achieved by applying a higher level of stimulation for a shorter pulse width time. Therefore, for applying a given charge to a patient, the cochlear implant system may have some flexibility by trading off the stimulation current level (i.e., the target stimulation voltage level) and the pulse width to achieve a desired charge while meeting system specifications.

Electrode impedance may represent a measure of how difficult it is (e.g., how much voltage is required) for a particular electrode at a particular stimulation site to push a particular amount of stimulation current into the patient at the particular stimulation site. Electrode impedance may be dependent on the physiological properties of the tissue where the electrode is implanted, the composition of the electrode itself, and/or various other factors. As such, electrode impedance may vary from patient to patient, from stimulation site to stimulation site within a given patient, and from day to day (or more often in certain situations).

Various factors may cause an electrode impedance of a particular electrode implanted within a particular patient to change. For example, changes in one or more physiological properties of tissue within the cochlea, aging, a change in body fat percentage, introduction of scar tissue, dehydration, and/or infection may lead to a change in electrode impedance. In the same or other examples, a change in electrode impedance may be caused by an electrode malfunction (e.g., an electrode may become shorted or open). Certain electrode impedance changes (e.g., those brought on by an episode of Meniere's disease, a middle ear effusion or other such infection, etc.) may be localized to a single ear, while other electrode impedance changes (e.g., those caused by a common cold or another such illness) may be more systemic, causing similar electrode impedance changes with respect to both ears. Similarly, certain electrode impedance changes (e.g., those caused by aging, etc.) may be permanent, while other electrode impedance changes (e.g., those caused by infections, etc.) may be temporary. In certain examples, variations in electrode impedance may occur predictably and/or cyclically. For example, certain patients may have different electrode impedances at different times during the day or during different seasons of the year, and so forth.

If electrode impedance changes are not detected and accounted for, the total charge applied to a patient at a given electrode may change in ways that are not known, are not accounted for, and/or are undesirable for proper operation of the cochlear implant system. For example, a current source that provides stimulation current may begin to operate outside of a normal compliance mode that the current source is designed to operate within. For instance, the current source may operate outside of a linear region (e.g., which may require progressively larger voltages to produce a particular current increase), and/or may apply voltages near or exceeding a maximum voltage (i.e., a "tank voltage") at which the current source is able to operate or designed to operate.

This change in total charge applied to various stimulation sites may have adverse effects on the cochlear implant system, such as by causing the cochlear implant system to stimulate the patient with inappropriate loudness levels, degraded sound quality, distorted pitch levels, and the like. As a result, such sound quality degradation may adversely affect the ability of the patient to recognize speech, music, and/or other sounds. This can be especially devastating for pediatric cochlear implant patients because the change in sound quality or volume may go unnoticed for long periods of time. Hence, an undetected change in electrode impedance can potentially interfere with the overall speech and language development of pediatric patients. Additionally, it will be recognized that cochlear implant patients of all ages may experience similar difficulties if a change in electrode impedance is not detected and accounted for.

Accordingly, it may be desirable for an apparatus associated with the cochlear implant system to periodically (e.g., during normal day-to-day operation rather than only at clinical checkup times) determine the electrode impedance of an electrode according to methods and techniques described herein for purposes of compensating for and/or otherwise responding to the electrode impedance measurements taken. For example, it may be desirable in some implementations for the apparatus to be configured to adjust stimulation parameters (e.g., pulse widths, stimulation current levels, target stimulation voltage levels, etc.) to maintain a total charge per phase applied to a stimulation site within the cochlea at a constant level. In the same or other implementations, it may be desirable for other impedance response operations to be performed, such as will be described in detail below.

Fortunately, by determining and responding to electrode impedances in the ways described herein, disclosed apparatuses and methods may provide these and/or various additional benefits. Specifically, apparatuses and methods described herein may allow for electrode impedances to be dynamically detected outside of a fitting session and/or outside of a clinical setting (e.g., when the patient is at home and during normal operation of the cochlear implant system, etc.). As a result, various operations responsive to the determining of the electrode impedance may be performed to provide various advantages to patients, medical professionals overseeing care of the patients (e.g., clinicians, etc.), caretakers of patients (e.g., parents of pediatric patients, etc.), and/or other people associated with cochlear implant systems.

For example, patients may avoid diminished sound quality and corresponding speech and language development effects in spite of unforeseeable circumstances (e.g., illnesses, infections, etc.) and other factors that cause electrode impedances to change. Moreover, responsive to determining electrode impedance, the apparatuses may be configured to automatically set cochlear implant system stimulation parameters in accordance with predetermined stimulation parameter adjustment constraints ("adjustment constraints") that may be designated by clinicians or other medical professionals. In this way, patients and caretakers may benefit from automatic improvements to cochlear implant system performance such as automatic increases in loudness levels to match corresponding decreases in perceived loudness levels that may accompany illness and/or other situations in which the hearing perception of the patient is altered. This may be significantly more convenient for the patients and/or caretakers than would be visiting a clinic in order to have electrode impedance manually analyzed and stimulation parameters manually set by professionals in the clinical setting.

At the same time, these automatic improvements may be performed in such a way that there continues to be professional oversight and safeguards in place to prevent the patient or the cochlear implant system from setting the stimulation parameters to inappropriate values, undesirable values, or values that are otherwise unapproved by the medical professional. For example, as will be described in more detail below, the medical professional may put adjustment constraints in place in accordance with which automatic stimulation parameter adjustment operations are performed. These benefits and other benefits of the apparatuses and methods described herein will be described and/or otherwise made apparent by the description of the various embodiments below.

Certain embodiments and principles will now be described with reference to the figures. It will be understood that the figures are not necessarily intended to exhaustively illustrate each and every embodiment of the apparatuses and methods described herein. Rather, the figures are configured to give context to and facilitate understanding of various principles and exemplary configurations by which the apparatuses and methods described herein may be implemented.

FIG. 1 illustrates an exemplary cochlear implant system 100. As shown, cochlear implant system 100 may include various components configured, in the example to FIG. 1, to be located external to a cochlear implant patient. These components include, but are not limited to, a microphone 102, a sound processor 104, and a headpiece 106. Cochlear implant system 100 may further include various components configured to be implanted within the patient in the example of FIG. 1, including, but not limited to, a cochlear implant 108 (also referred to as an implantable cochlear stimulator) and a lead 110 (also referred to as an intracochlear electrode array) with a plurality of electrodes 112 disposed thereon. In certain examples, additional or alternative components may be included within cochlear implant system 100 as may serve a particular implementation. The components shown in FIG. 1 will now be described in more detail.

Microphone 102 may be configured to detect audio signals presented to the patient and to generate electrical signals representative of the detected audio signals (e.g., for processing by sound processor 104). Microphone 102 may be implemented in any suitable manner. For example, microphone 102 may include a microphone such as a T-MIC™ microphone from Advanced Bionics. Microphone 102 may be associated with a particular ear of the patient such as by being located in a vicinity of the particular ear (e.g., within the concha of the ear near the entrance to the ear canal). In some examples, microphone 102 may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone or microphones as may serve a particular implementation.

Sound processor 104 may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. While, for the sake of simplicity, electrical stimulation will be described herein as being applied to one or both of the cochleae of a patient, it will be understood that stimulation current may also be applied to other suitable nuclei in the auditory pathway. To this end, sound processor 104 may process the one or more audio signals in accordance with a selected sound processing program (e.g., a strategy or program for generating appropriate stimulation parameters for controlling cochlear implant 108, as will be described in more detail below). Sound processor 104 may include or be implemented by a behind-the-ear ("BTE") unit, a body worn device, and/or any other sound processing unit as may serve a particular implementation. In certain examples, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or power signals to cochlear implant 108 by way of a wireless communication link 114 (e.g., a transcutaneous link) between headpiece 106 and cochlear implant 108. It will be understood that communication link 114 may include a bidirectional communication link and/or one or more dedicated unidirectional communication links. In some examples, sound processor 104 may execute and operate in accordance with a sound processing program that has been loaded into memory contained within sound processor 104.

In order to perform the operations described above, sound processor 104 may include one or more physical computing components (e.g., processors, memory resources, communication interfaces, etc.) enabling sound processor 104 to function as a primary processing center for cochlear implant system 100. Additionally, using these one or more physical computing components, sound processor 104 may implement any of the exemplary apparatuses for acquiring and using cochlear implant electrode impedance measurements described herein and/or may perform any of the operations (e.g., impedance response operations) that will be described in more detail below. In particular, as will be described below, sound processor 104 may implement an apparatus for setting cochlear implant system stimulation parameters based on electrode impedance measurements.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, wireless data signals and/or wireless power may be wirelessly transmitted between sound processor 104 and cochlear implant 108 via communication link 114.

Cochlear implant 108 may include any type of implantable stimulator that may be used in association with the apparatuses, systems, and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously or concurrently by way of multiple electrodes 112.

As mentioned above, and as will be described in more detail below, each electrode 112 may be associated with an electrode impedance that may be determined at one point in time (e.g., by a clinician during a clinical fitting session of cochlear implant system 100 to a patient) but may subsequently change. As such, the electrode impedances of electrodes 112 may be determined periodically using the apparatuses and methods described herein, thereby triggering any of various types of responses to be performed by the apparatuses described herein when an electrode impedance change is detected.

Figure 2:
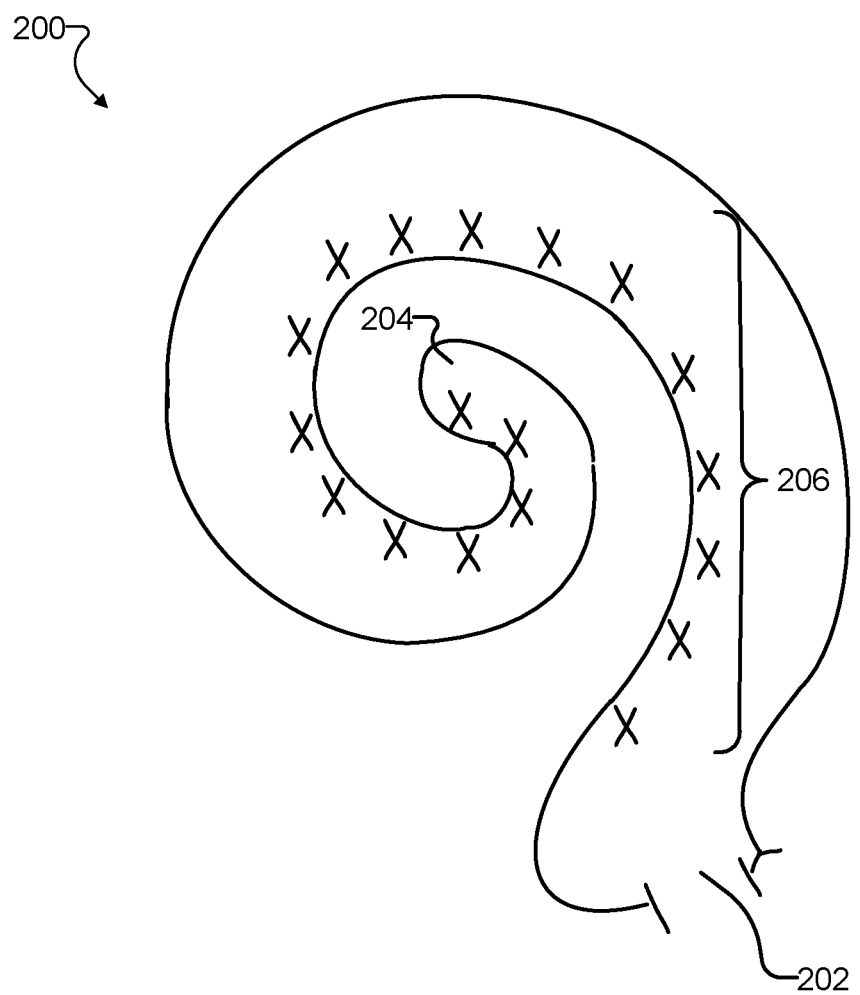
FIG. 2 illustrates a schematic structure of the human cochlea according to principles described herein.

FIG. 2 illustrates a schematic structure of the human cochlea 200 into which lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. Auditory nerve tissue 206 is organized within cochlea 200 in a tonotopic manner. That is, relatively low frequencies are encoded at or near apex 204 of cochlea 200 (referred to as an "apical region") while relatively high frequencies are encoded at or near base 202 (referred to as a "basal region"). Hence, each location along the length of cochlea 200 corresponds to a different perceived frequency. Cochlear implant system 100 may therefore be configured to apply electrical stimulation to different locations within cochlea 200 (e.g., different locations along auditory nerve tissue 206) to provide a sensation of hearing to the patient. For example, when lead 110 is properly inserted into cochlea 200, each of electrodes 112 may be located at a different cochlear depth within cochlea 200 (e.g., at a different part of auditory nerve tissue 206) such that stimulation current applied to one electrode 112 may cause the patient to perceive a different frequency than the same stimulation current applied to a different electrode 112 (e.g., an electrode 112 located at a different part of auditory nerve tissue 206 within cochlea 200).

Conventionally, specialized equipment used by a clinician and/or other medical professional in a clinical-type setting (e.g., a cochlear implant programming system such as a clinician's programming interface ("CPI") device) may be communicatively coupled to cochlear implant system 100 to program cochlear implant system 100, to fit cochlear implant system 100 to a patient, and/or to otherwise set and adjust the operation of cochlear implant system 100 with respect to the patient. For example, under direction of the clinician, one or more stimulation parameters (e.g., charge levels, stimulation levels, stimulation pulse widths, etc.) may be set or revised, one or more sound processing programs may be updated or newly loaded onto sound processor 104, and so forth.

Unfortunately, as mentioned above, electrode impedances may change between patient visits to the clinic, causing cochlear implant system 100 to provide reduced sound quality, to malfunction, or to otherwise operate less effectively than desired. Accordingly, it may be desirable for patients and/or other persons associated with the patients other than the clinicians (e.g., parents, caregivers, etc.) to have at least some visibility and/or control over basic parameters of the functionality of cochlear implant system 100. For example, it may be desirable, outside of a clinical setting, for cochlear implant system 100 to determine and monitor electrode impedances of the electrodes implanted within the patient, and to respond to certain electrode impedances or changes in electrode impedance by performing certain operations (e.g., setting stimulation parameters) automatically and/or with user input from the patient or another user. Such extra-clinical visibility and/or control of cochlear implant system 100 may be provided to the patient and/or other persons by way of various apparatuses and methods described herein.

Figure 3:
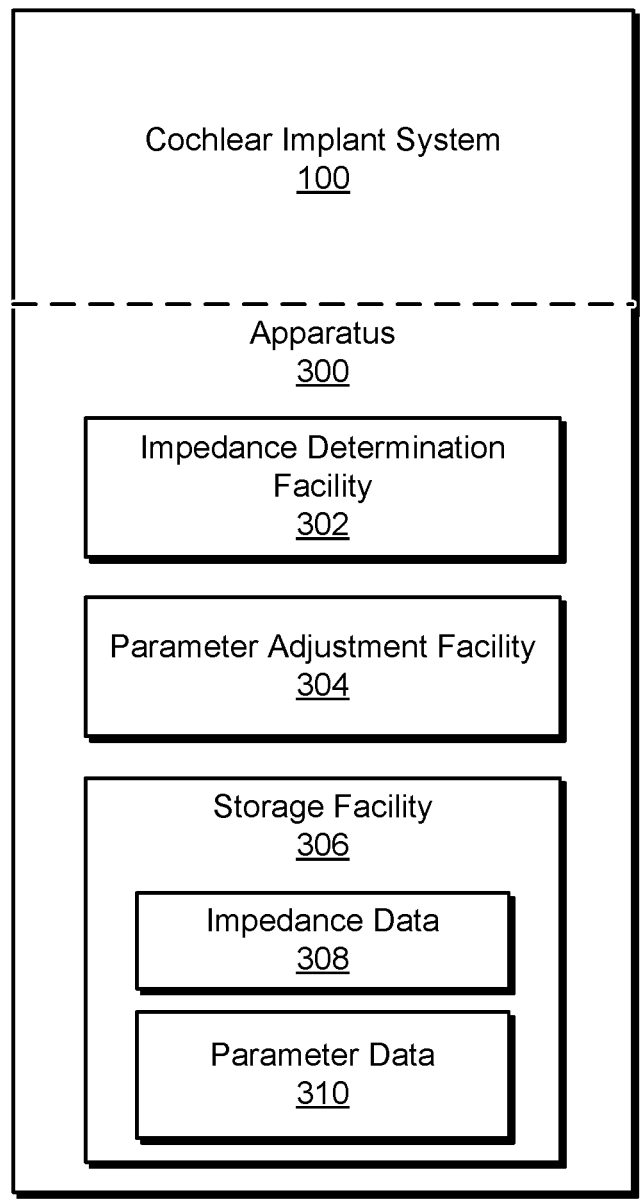
FIG. 3 illustrates an exemplary apparatus for setting cochlear implant system stimulation parameters based on electrode impedance measurements according to principles described herein.

For example, FIG. 3 illustrates an exemplary apparatus 300 for setting cochlear implant system stimulation parameters based on electrode impedance measurements according to principles described herein. As shown, apparatus 300 may be associated with a cochlear implant system. The cochlear implant system associated with apparatus 300 in FIG. 3 is shown to be cochlear implant system 100. However, it will be understood that other types of cochlear implant systems described herein that may be different from cochlear implant system 100 (e.g., fully implantable cochlear implant systems, etc.) may similarly be associated with apparatus 300 in other implementations.

The association between apparatus 300 and cochlear implant system 100 (illustrated by a dashed line in FIG. 3) may take any of various suitable forms. For instance, apparatus 300 may be implemented by various components that are either part of cochlear implant system 100 or that are separate from, but communicatively coupled with, cochlear implant system 100. Thus, for example, apparatus 300 may be implemented by sound processor 104 within cochlear implant system 100, by cochlear implant 108 within cochlear implant system 100, by a mobile computing device communicatively coupled to cochlear implant system 100, or by any other suitable apparatus associated with cochlear implant system 100 as may serve a particular implementation.

As shown, apparatus 300 may include, without limitation, an impedance determination facility 302, a parameter adjustment facility 304, and a storage facility 306 selectively and communicatively coupled to one another. It will be recognized that although facilities 302 through 306 are shown to be separate facilities in FIG. 3, facilities 302 through 306 may be combined into fewer facilities, such as into a single facility, or divided into more facilities as may serve a particular implementation. Each of facilities 302 through 306 will now be described in more detail.

Impedance determination facility 302 may include one or more physical computing components (e.g., hardware and/or software components such as a processor, a memory, a communication interface, instructions stored on the memory for execution by the processor, etc.) that are associated with (e.g., are included within, are communicatively coupled with, etc.) cochlear implant system 100. Using the one or more physical computing components, impedance determination facility 302 may perform any of various operations to determine an electrode impedance for at least one of electrodes 112 included in cochlear implant system 100. For example, impedance determination facility 302 may direct cochlear implant 108 (which is implanted within the patient) to generate electrical stimulation current at a predetermined current level, and to apply the electrical stimulation current to the patient by way of a particular electrode 112 coupled with cochlear implant 108. Impedance determination facility 302 may further direct cochlear implant 108 to measure a voltage level associated with the electrode 112 while the electrical stimulation current is applied to the patient by way of the electrode 112. Then, based on the predetermined current level and the measured voltage level, impedance determination facility 302 may determine an impedance of the electrode 112 in any of the ways described herein (e.g., by dividing the measured voltage level by the predetermined currently level in accordance with Ohm's Law).

Parameter adjustment facility 304 may similarly include one or more physical computing components (e.g., the same or separate hardware and/or software components as impedance determination facility 302) that are configured to identify an adjustment constraint and/or to automatically adjust (e.g., based on the impedance of the electrode 112 and in accordance the predetermined stimulation parameter adjustment constraint that is identified) a stimulation parameter associated with cochlear implant system 100. Parameter adjustment facility 304 may perform these and/or other suitable operations in any manner as may serve a particular implementation. For instance, as will be described below, the adjustment constraint may be determined and set within storage facility 306 by a medical professional facilitating care of the patient with respect to the cochlear implant system (e.g., by a clinician during a regular clinical visit), and parameter adjustment facility 304 may identify the adjustment constraint by retrieving it from storage facility 306.

As parameter adjustment facility 304 adjusts a stimulation parameter associated with the adjustment constraint (e.g., automatically or under direction of a user of apparatus 300 such as the patient), parameter adjustment facility 304 may ensure that the adjustments are performed in accordance with the adjustment constraint. For instance, if the adjustment constraint represents a maximum value for the stimulation parameter, parameter adjust facility 304 may ensure that the stimulation parameter value does not exceed the maximum value of the adjustment constraint as the stimulation parameter is adjusted.

Storage facility 306 may maintain any suitable data received, generated, managed, maintained, used, and/or transmitted by facilities 302 or 304 in a particular implementation. For example, as shown, storage facility 306 may include impedance data 308, which may include data associated with determining electrode impedances such as stimulation levels (e.g., patient specific stimulation levels), predetermined current levels (e.g., impedance test current levels) that are to be applied to the patient, electrode voltage levels, electrode impedance levels, and/or any other data as may facilitate facilities 302 and 304 in performing the operations described herein. Similarly, storage facility 306 may include parameter data 310, which may include data associated with one or more adjustment constraints (e.g., set by a clinician as described above), data associated with current stimulation parameter values, data associated with predetermined adjustment timelines, and/or any other data for performing one or more of the operations described herein. Storage facility 306 may also maintain additional or alternative data as may serve a particular implementation.

Using facilities 302 through 306 together with methods and techniques described herein, apparatus 300 may adjust stimulation parameters in accordance with adjustment constraints in any manner as may serve a particular implementation. For instance, apparatus 300 may identify an adjustment constraint, and, based on the impedance of the electrode and in accordance with the adjustment constraint, may automatically adjust a stimulation parameter associated with the cochlear implant system. In some examples, the adjustment constraint may be a clinician-imposed constraint, a time limit, a constraint associated with user input from the patient, or the like. As such, a stimulation parameter such as a pulse width time period during which stimulation is applied may not be adjusted completely or all at once in response to the determination of the electrode impedance, but, rather, may be adjusted partially and/or gradually according to the adjustment constraint.

As described above, various benefits may result from apparatus 300 identifying the adjustment constraint and/or automatically adjusting the stimulation parameter in accordance with the adjustment constraint. In addition to benefits described above, it will be understood that apparatus 300 may further provide additional benefits associated with certain adjustment constraints and/or ways of automatically adjusting the stimulation parameter in accordance therewith. In particular, it may be disorienting (e.g., surprising, jarring, distracting, etc.) to a patient if particular stimulation parameters (e.g., pulse width, stimulation levels, stimulation rate, numbers of active electrodes, etc.) change too much, too quickly, and/or without warning. As a result, while it may be desirable for stimulation parameters to be automatically adjusted based on measurements (e.g., electrode impedance measurements) that are performed during normal operation of the cochlear implant system, it may be desirable for such automatic adjustments to be made in a controlled and/or gradual manner, and/or with some degree of oversight of qualified medical personnel (e.g., a clinician overseeing the patient's care with respect to the cochlear implant system). Such control and non-disorienting automatic adjustments may be implemented by identifying an adjustment constraint and automatically adjusting the stimulation parameter in accordance with (e.g., only in accordance with) the adjustment constraint.

An adjustment constraint may be generated, controlled, and/or otherwise set by any suitable party and may represent any suitable type of constraint as may serve a particular implementation. For example, the adjustment constraint may be set by a medical professional facilitating care of the patient with respect to the cochlear implant system such as a clinician, surgeon, audiologist, or the like. As such, the adjustment constraint may represent an upper bound under which the stimulation parameter is to remain during the automatic adjustment of the stimulation parameter, a lower bound above which the stimulation parameter is to remain during the automatic adjustment of the stimulation parameter, a range within which the stimulation parameter is to remain during the automatic adjustment of the stimulation parameter, and/or another suitable adjustment constraint. In some examples, the adjustment constraint may relate to a particular electrode, while in other examples, the adjustment constraint may relate to a plurality of (e.g., all of) the electrodes included within the cochlear implant system. Exemplary adjustment constraints will be described and illustrated in more detail below.

Moreover, as will further be described and illustrated, the stimulation parameter automatically adjusted in accordance with the adjustment constraint may similarly be any parameter as may serve a particular implementation. For example, the stimulation parameter may be a pulse width associated with stimulation pulses applied to the patient by way of the electrode during a normal operation of the cochlear implant system. In other examples, the stimulation parameter may be a stimulation level such as a target stimulation voltage value associated with stimulation pulses applied to the patient (e.g., associated with a stimulation current level at which current stimulation pulses are applied), a stimulation rate (e.g., a time period during which a stimulation phase is completed for which each of the electrode channels of the cochlear implant), a parameter related to an active number of electrode (e.g., how many electrodes may be in active use versus disabled or otherwise shut off), or another suitable stimulation parameter.

As will be described and illustrated in more detail below, in some examples, a plurality of stepwise values between an initial value of the stimulation parameter and a target value of the stimulation parameter may be set up instead of capping (e.g., setting a maximum, minimum, or range of values for) the stimulation parameter. Thus, for example, rather than moving to the target value all at once, the user may be able to move toward the target value when the user feels prepared to make such movements to avoid the inconvenience and other disorienting drawbacks of changing the stimulation parameter too fast. More particularly, the adjustment constraint may be associated with user input manually provided by the patient to the cochlear implant system. The adjustment constraint may represent a particular stepwise value in a plurality of stepwise values between an initial value and a target value to which the stimulation parameter (e.g., a pulse width associated with stimulation pulses applied to the patient by way of the electrode during normal operation of the cochlear implant system, or the like) is automatically adjusted based on the user input to facilitate a gradual adjustment of the stimulation parameter from the initial value to the target value.

Similarly, in the same or other examples, the adjustment constraint may be associated with a predetermined adjustment timeline set by the patient, a caretaker of the patient, the medical professional, or another such user of the cochlear implant system. As such, the predetermined adjustment timeline may specify a plurality of automatic stepwise adjustments associated with the stimulation parameter (e.g., a pulse width associated with stimulation pulses applied to the patient by way of the electrode during normal operation of the cochlear implant system) to facilitate a gradual adjustment of the stimulation parameter from an initial value to a target value. However, in contrast with the example above, the gradual adjustments may be made automatically at designated time intervals, rather than based on user input. For example, designated time intervals (e.g., a number of minutes, hours, days, etc.) may be inserted between the automatic stepwise adjustments in the plurality of automatic stepwise adjustments associated with the stimulation parameter.

In some implementations, rather than inserting designated time intervals between automatic stepwise adjustments, automatic adjustments may be made based on other factors. For instance, automatic stepwise adjustments such as those described above may be made at designated times of day or night when patients are less likely to notice or be affected by the adjustments. For example, the automatic adjustment of the stimulation parameter may be performed only during a powering-up sequence of cochlear implant system 100 in accordance with the adjustment constraint (e.g., based on an instruction included within or otherwise associated with the adjustment constraint). In this way, the automatic adjustment (e.g., whether a stepwise adjustment or a full adjustment to the target value) may be made prior to a patient using the cochlear implant system on a given day (e.g., when he or she wakes up in the morning and powers on his or her cochlear implant system). As with other adjustment constraints described herein, this type of adjustment constraint may facilitate making automatic adjustments to the stimulation parameter less noticeable, less disorienting, and/or otherwise less detrimental to the patient's hearing experience.

In some examples, apparatus 300 may automatically adjust the stimulation parameter by automatically directing (e.g., based on the impedance of the electrode 112 determined by impedance determination facility 302) sound processor 104 within the cochlear implant system 100 to switch from operating in accordance with a first sound processing program to operating in accordance with a second sound processing program.

As mentioned above, cochlear implant system sound processors such as sound processor 104 may operate in accordance with particular sound processing programs by, for example, directing a cochlear implant (e.g., cochlear implant 108) to apply stimulation to the patient in accordance with the sound processing program. As used herein, a "sound processing program" may refer to any data stored within and/or used by a sound processor. In particular, sound processing programs may refer to datasets (e.g., files, etc.) including personalized and/or customized data associated with a particular cochlear implant within the cochlear implant system.

In some examples, a sound processing program may represent a particular program (e.g., stimulation parameters, methodologies, techniques, etc.) by which an incoming audio signal is to be processed and prepared prior to being used by the particular cochlear implant to stimulate the patient. For example, a sound processing program may include a discrete dataset that is customized to direct the particular cochlear implant in accordance with unique needs and/or preferences of a patient using the cochlear implant in different types of listening environments. Specifically, for instance, different electrical parameters, channel mappings, dynamic ranges, electrode settings, microphone directionality settings, and/or other stimulation parameters and settings may be set in different sound processing programs to optimize the operation of the cochlear implant for relatively noisy or relatively quiet listening environments, for relatively large or relatively small rooms (e.g., having more or less echo and/or reverberation), for listening to music, for listening to speech, for listening to an auxiliary audio input, and/or for any other listening scenario or listening environment as may serve a particular implementation.

Apparatus 300 may automatically direct the sound processor to switch from operating in accordance with the first sound processing program to operating in accordance with the second sound processing program based on the determined impedance of the electrode for any suitable reason. For example, apparatus 300 may determine, based on the electrode impedance, that the patient is experiencing an altered hearing episode, and may switch the sound processing program to help compensate for effects of the altered hearing episode.

An altered hearing episode may include any temporary illness, infection, or other type of episode that may cause a temporary effect on the electrode impedances of one or more electrodes implanted within the patient. For instance, a patient suffering from Meniere's disease may periodically experience Meniere's episodes characterized by vertigo, tinnitus, hearing loss, and/or other symptoms. Leading up to and during a Meniere's episode, electrode impedances of one or more electrodes implanted in the patient may change significantly from normal impedance levels, causing various problems for the patient as described above. However, subsequent to the Meniere's episode (e.g., immediately or after a period of time) the electrode impedances may return back to normal levels. Other types of episodes having other causes such as a common cold (i.e., common cold episodes), a middle ear effusion (i.e., middle ear effusion episodes), and the like may cause similar temporary changes to the patient's electrode impedances.

In some examples, a patient prone to such altered hearing episodes may be given (e.g., the patient's sound processor may be programmed to include) one or more specialized sound processing programs configured to improve hearing during the altered hearing episodes. However, in order to make use of these sound processing programs, such patients have conventionally had to determine that they are having an altered hearing episode serious enough to warrant switching sound processing programs and manually cause the sound processor to switch sound processing programs. Besides the inconvenience of having to switch sound processing programs manually in this way, the manual switching of sound processing programs has other drawbacks. In certain examples, a patient may manually switch sound processing programs and find out that the switch does not improve their hearing (e.g., because the sound processing program selected is not configured to improve hearing for the type of altered hearing episode the patient believed he or she was experiencing, the altered hearing episode is not serious enough to warrant switching sound processing programs, etc.). In other examples, the patient may simply forget or not bother to manually switch sound processing programs (e.g., especially if the change in hearing due to the altered hearing episode comes on gradually so as to be unnoticeable), may select a wrong sound processing program, or the like. Even if the patient selects the proper sound processing program to switch to at the proper time, it may be difficult to adjust the volume with respect to the new sound processing program such that sounds are perceived at the same volume levels that the patient perceived with the previous sound processing program.

Accordingly, apparatus 300 may overcome these and other drawbacks by automatically directing the sound processor to switch from the first to the second sound processing program based on the determined electrode impedance. Specifically, apparatus 300 may determine that the patient is experiencing an altered hearing episode during which a volume perceived by the patient of stimulation presented to the patient by the cochlear implant is different from a first applied volume at which the stimulation is presented. Based on the determination that the patient is experiencing the altered hearing episode, apparatus 300 may select the second sound processing program to improve hearing for the patient from the first sound processing program. Finally, apparatus 300 may automatically direct the sound processor to switch from operating in accordance with the first sound processing program to operating in accordance with the second sound processing program such that the stimulation presented to the patient by the cochlear implant when the sound processor operates in accordance with the second sound processing program is presented at a second applied volume different from the first applied volume, where the second applied volume causes the volume perceived by the patient to match the first applied volume. In other words, the patient may automatically perceive sound at the same volume and in the same way after the electrode impedance effects of the altered hearing episode set in as before the effects set in.

In other examples, the volume at which the patient perceives sound may intentionally be changed along with the sound processing program. For example, loud sounds may be especially harsh to a patient experiencing a Meniere's episode. As such, apparatus 300 may direct the cochlear implant system to present sounds at a quieter volume that may be more pleasant to the patient during the Meniere's episode.

In some examples, apparatus 300 may automatically direct the sound processor to switch from operating in accordance with the first sound processing program to operating in accordance with the second sound processing program to avoid a situation in which the cochlear implant system operates outside of a normal compliance mode. Specifically, apparatus 300 may determine (e.g., based on the determined impedance of the electrode) that the cochlear implant system is operating outside of the normal compliance mode, and may automatically direct the sound processor to switch from operating in accordance with the first sound processing program to operating in accordance with the second sound processing program further based on the determination that the cochlear implant system is operating outside of the normal compliance mode.

As described above, a cochlear implant system may be said to operate outside of a normal compliance mode when the cochlear implant system applies voltages or currents that exceed the bounds of operating specifications under which the cochlear implant system is designed to operate. For example, a cochlear implant system that applies target stimulation voltages at or above a voltage level designated as a maximum voltage level or tank voltage level that the cochlear implant system is to use during operation in order to apply a particular charge to a particular stimulation site within the patient may be operating outside of the normal compliance mode.

Accordingly, apparatus 300 may determine, based on the measuring of a voltage level associated with the electrode by impedance determination facility 302 as part of the determination of the electrode impedance, that the measured voltage level has reached a maximum voltage that the cochlear implant is configured to apply. Based on the determination that the measured voltage level has reached the maximum voltage that the cochlear implant is configured to apply, apparatus 300 may determine that the cochlear implant system is operating outside of the normal compliance mode.

As will be described in more detail below, in some examples, apparatus 300 may generate an alert that is associated with the impedance of the electrode and is adapted for presentation to a user associated with the cochlear implant system (e.g., the patient, a caretaker of the patient, a clinician who works with the patient, etc.). For instance, apparatus 300 may generate the alert in response to the determination of the impedance of the electrode in conjunction with, instead of, or in addition to, making the automatic adjustment to the stimulation parameter associated with cochlear implant system 100 (e.g., directing the sound processor to switch from operating in accordance with the first sound processing program to operating in accordance with the second sound processing program and/or by other suitable operations).

As mentioned above, apparatus 300 may be implemented and/or associated with cochlear implant system 100 in various suitable ways. For instance, referring to the configuration of cochlear implant system 100 illustrated in FIG. 1, apparatus 300 may be implemented by (e.g., included within) sound processor 104 external to the patient. In other examples, however, apparatus 300 may be implemented by other external devices that are separate from and communicatively coupled with cochlear implant system 100, by components of cochlear implant system 100 that are implanted within the patient, and/or by other suitable devices and/or components as may serve a particular implementation.

Figure 4:
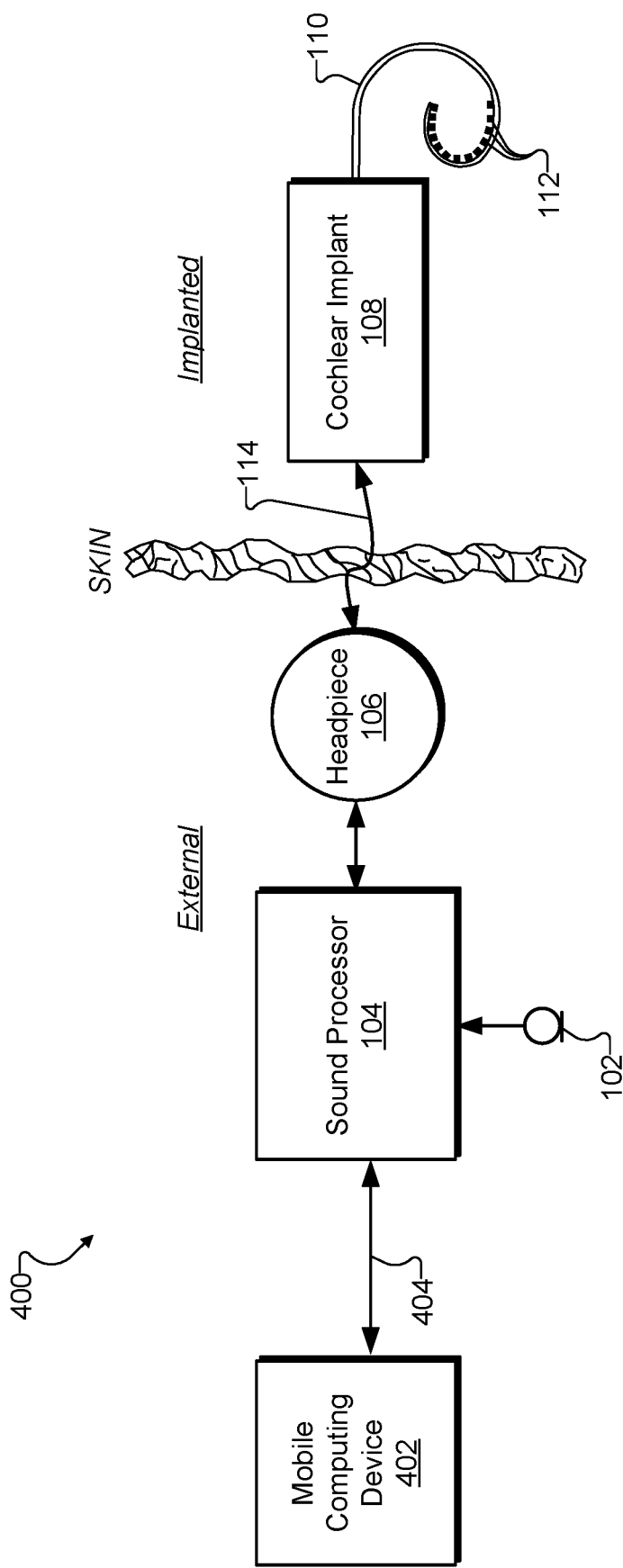
FIG. 4 illustrates an exemplary configuration in which the apparatus of FIG. 3 may be implemented according to principles described herein.
Figure 5:
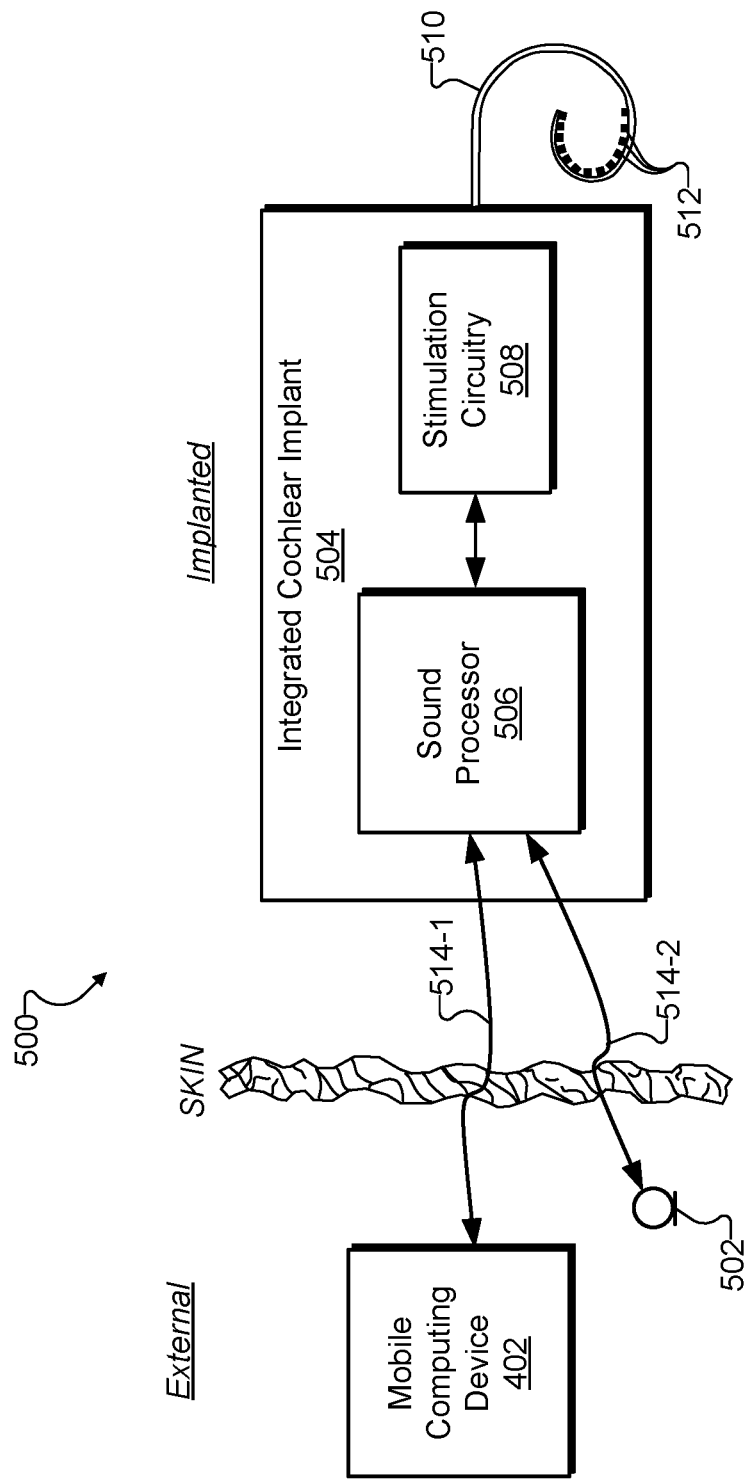
FIG. 5 illustrates another exemplary configuration in which the apparatus of FIG. 3 may be implemented according to principles described herein.

To illustrate, FIGS. 4 and 5 show different exemplary configurations in which apparatus 300 may be implemented. Specifically, FIG. 4 illustrates an exemplary configuration 400 in which an exemplary mobile computing device 402 that is separate from cochlear implant system 100 is also communicatively coupled with cochlear implant system 100. Rather than being implemented by a component of cochlear implant system 100 such as sound processor 104, apparatus 300 may be implemented by mobile computing device 402. For example, at least one physical computing component included within mobile computing device 402 may perform the operations described herein as being performed by apparatus 300. In some examples, apparatus 300 may also be implemented partially by both mobile computing device 402 and by a component of cochlear implant system 100 such as sound processor 104.

Mobile computing device 402 may be owned and/or operated by the patient and/or other persons associated with the patient (e.g., caregivers, etc.) in any suitable location and/or at any suitable time. For example, mobile computing device 402 may be used to facilitate operating and controlling cochlear implant system 100 outside of a clinical setting while cochlear implant system 100 is being used by the patient in a normal operating mode.

Mobile computing device 402 may be implemented by any type of computing device as may serve a particular implementation. For instance, mobile computing device 402 may be implemented as a general-purpose smartphone, tablet computing device, or other such mobile device (e.g., executing a specific application ("app") associated with cochlear implant system 100) that is operated by the patient or a caregiver of the patient. In certain examples, mobile computing device 402 may also be implemented by computing devices that are less portable (e.g., laptop or desktop computers, etc.) or by specialized devices dedicated to performing the operations described herein (e.g., special accessory devices associated with cochlear implant system 100).

As shown, mobile computing device 402 may be communicatively coupled with cochlear implant system 100 (and with sound processor 104 in particular) by way of a connection 404. Connection 404 may be a wireless or a wired connection, and may use any communication protocol as may serve a particular implementation. For example, connection 404 may be a wireless Bluetooth connection, a wireless Wi-Fi connection, a wireless near-field communication ("NFC") connection, a wired Universal Serial Bus ("USB") connection, a proprietary wired or wireless connection, or another such connection that suitably couples mobile computing device 402 with cochlear implant system 100. Once mobile computing device 402 is communicatively coupled with cochlear implant system 100 (e.g., with sound processor 104) as illustrated in configuration 400, mobile computing device 402 may implement apparatus 300 and/or any other implementation of an apparatus for setting cochlear implant system stimulation parameters based on electrode impedance measurements described herein.

As mentioned above, because sound processor 104 and mobile computing device 402 may both include physical computing components, either of sound processor 104 and mobile computing device 402 may implement apparatus 300 alone, or sound processor 104 and mobile computing device 402 may operate together to implement apparatus 300. In other examples, additional components associated with cochlear implant system 100 may also implement the apparatus (e.g., alone or together with sound processor 104 and/or mobile computing device 402). For example, in certain implementations, cochlear implant 108 may fully or partially implement apparatus 300 and may perform at least some of the operations described herein for setting cochlear implant system stimulation parameters based on electrode impedance measurements. Such implementations may be particularly advantageous, for example, for a cochlear implant that is implemented as an integrated cochlear implant (i.e., a cochlear implant that includes one or more physical computing components performing operations analogous to a sound processor) in a fully implantable cochlear implant system (i.e., a cochlear implant system that is fully (or nearly fully) implanted within the patient).

To illustrate this type of implementation, FIG. 5 shows an exemplary configuration that includes an exemplary cochlear implant system 500 that is configured to perform a similar role as cochlear implant system 100. As such, it will be understood that cochlear implant system 500 may be associated with apparatus 300 in certain implementations in place of cochlear implant system 100.

Similar to cochlear implant system 100, cochlear implant system 500 includes components such as a microphone 502 (analogous to microphone 102), an integrated cochlear implant 504 that includes a sound processor 506 and stimulation circuitry 508 (analogous to sound processor 104, headpiece 106, and cochlear implant 108), an electrode lead 510 with a plurality of implanted electrodes 512 (analogous to electrode lead 110 with electrodes 112), and transcutaneous wireless communication links 514 (i.e., wireless communication links 514-1 and 514-2, which are analogous to wireless communication link 114). As illustrated, cochlear implant system 500 is also communicatively coupled with mobile computing device 402 (e.g., coupled with sound processor 506 within integrated cochlear implant 504).

A significant difference between cochlear implant system 100 and cochlear implant system 500 is that cochlear implant system 500 is implemented as a fully implantable cochlear implant system. In particular, as shown, the functionality described above with respect to sound processor 104 has been moved from being external to the patient to being implemented within sound processor 506, which is implanted within the patient as part of integrated cochlear implant 504. The only component of cochlear implant system 500 not implanted within the patient is microphone 502, which may remain external to the patient (e.g., and communicate with sound processor 506 by way of wireless communication link 514-2) in order to detect sounds presented to the patient as clearly as possible.

In the example of FIG. 5, mobile computing device 402 may be communicatively coupled with integrated cochlear implant 504 (e.g., with sound processor 506 within integrated cochlear implant 504 in particular) by way of wireless communication link 514-1. In some examples, wireless communication link 514-1 may be implemented by any of the wireless types of connection 404 between mobile computing device 402 and sound processor 104 described above (e.g., Bluetooth, Wi-Fi, NFC, a proprietary wireless link, etc.). In other examples, wireless communication link 514-1 may be implemented more similarly to wireless communication link 114, described above in relation to FIG. 1. For example, cochlear implant system 500 may include a headpiece external to the patient and configured to couple with integrated cochlear implant 504 to communicate data, transmit operating power to recharge an implanted battery of integrated cochlear implant 504, and the like. In this example, mobile computing device 402 may communicate with integrated cochlear implant 504 by connecting (e.g., by way of a wired connection) with the headpiece and transmitting data transcutaneously in the manner described above with respect to headpiece 106 and cochlear implant 108.

In any case, once mobile computing device 402 is communicatively coupled with cochlear implant system 500 (e.g., with sound processor 506 within integrated cochlear implant 504), any of mobile computing device 402, integrated cochlear implant 504, sound processor 506, or a combination of these operating in tandem may serve to implement apparatus 300. As such, any of these components or any suitable combination thereof may perform the operations described herein for setting cochlear implant system stimulation parameters based on electrode impedance measurements.

For example, in an implementation in which integrated cochlear implant 504 implements apparatus 300, integrated cochlear implant 504 may include (e.g., as part of stimulation circuitry 508) a stimulation current generator configured to generate electrical stimulation current to be applied to the patient by way of an electrode 512 on electrode lead 510, and may further include a voltage detector configured to measure a voltage level associated with the electrode. As such, at least one physical computing component further included within integrated cochlear implant 504 may be configured to direct the stimulation current generator to generate electrical stimulation current at a predetermined current level and to apply the electrical stimulation current to the patient by way of the electrode, direct the voltage detector to measure the voltage level associated with the electrode 512 while the electrical stimulation current is applied to the patient by way of the electrode 512, determine (e.g., based on the predetermined current level and the measured voltage level) an impedance of the electrode 512, identify an adjustment constraint, and automatically adjust (e.g., based on the impedance of the electrode 512 and in accordance with the adjustment constraint) a stimulation parameter associated with cochlear implant system 500.

Regardless of how an apparatus for setting cochlear implant system stimulation parameters based on electrode impedance measurements is implemented with respect to a cochlear implant system (e.g., however apparatus 300 is implemented with respect to cochlear implant system 100, cochlear implant system 500, mobile computing device 402, or the like), the apparatus may be configured to set (e.g., automatically adjust) any of various stimulation parameters in response to electrode impedance measurements that are made during normal operation of the cochlear implant system. However, as mentioned above, the apparatus may be required to make certain tradeoffs in determining which stimulation parameters to set and/or how to set them.

For example, based on an electrode impedance measurement, apparatus 300 may determine that the electrode impedance has increased, likely resulting in the patient perceiving a lower loudness level for a given stimulation level and pulse width (i.e., a given charge level). As such, it may be desirable for apparatus 300 to adjust (e.g., automatically adjust) a stimulation parameter to increase the loudness level that the patient will perceive. The loudness level may be increased by way of adjustments to various different stimulation parameters. For instance, the loudness level may be increased by way of adjustments to the pulse width associated with stimulation pulses applied to the patient (e.g., by lengthening the pulse width), adjustments to the target stimulation voltage level associated with the stimulation pulses applied to the patient (e.g., by increasing the stimulation current to thereby increase the target stimulation voltage), adjustments to the number of active electrodes applying the stimulation pulses to the patient, or the like. However, each type of adjustment that may be made to improve system performance (e.g., to increase the loudness level in this example) may also risk degrading system performance in other ways if adjusted too far.

Specifically, for instance, as the pulse width gets longer the overall stimulation rate or pulse rate (i.e., the number of pulses applied per active channel per unit of time) decreases, thereby potentially degrading sound quality perceived by the user if the pulse width gets too long. As another example, as the target stimulation voltage level gets larger, the battery life of the system decreases, thereby potentially expending the battery so quickly that the battery cannot suitably sustain a charge to power the cochlear implant system between typical battery charging periods.

Accordingly, apparatus 300 may be configured to adjust stimulation parameters in a way that intelligently accounts for these types of tradeoffs so that certain aspects of system performance may be improved (e.g., the loudness level may be increased in the example above) without significantly degrading other important aspects (e.g., without noticeably degrading the sound quality or battery life of the system). Adjusting stimulation parameters in light of these tradeoffs may be done in any manner as may serve a particular implementation.

For example, apparatus 300 may adjust the stimulation parameters in accordance with adjustment constraints that have been identified by apparatus 300 in any of the ways described herein. For instance, adjustment constraints may have been previously set (e.g., within storage facility 306 of apparatus 300) by medical professionals, and/or by patients and/or caretakers themselves. Additionally or alternatively, apparatus 300 may adjust the stimulation parameters based on user input (e.g., from patients and/or caretakers of the patient) to make additional adjustments to the stimulation parameters. To illustrate, various exemplary aspects of how apparatus 300 may set (e.g., automatically adjust) various different types of stimulation parameters will now be described and illustrated.

Figure 6:
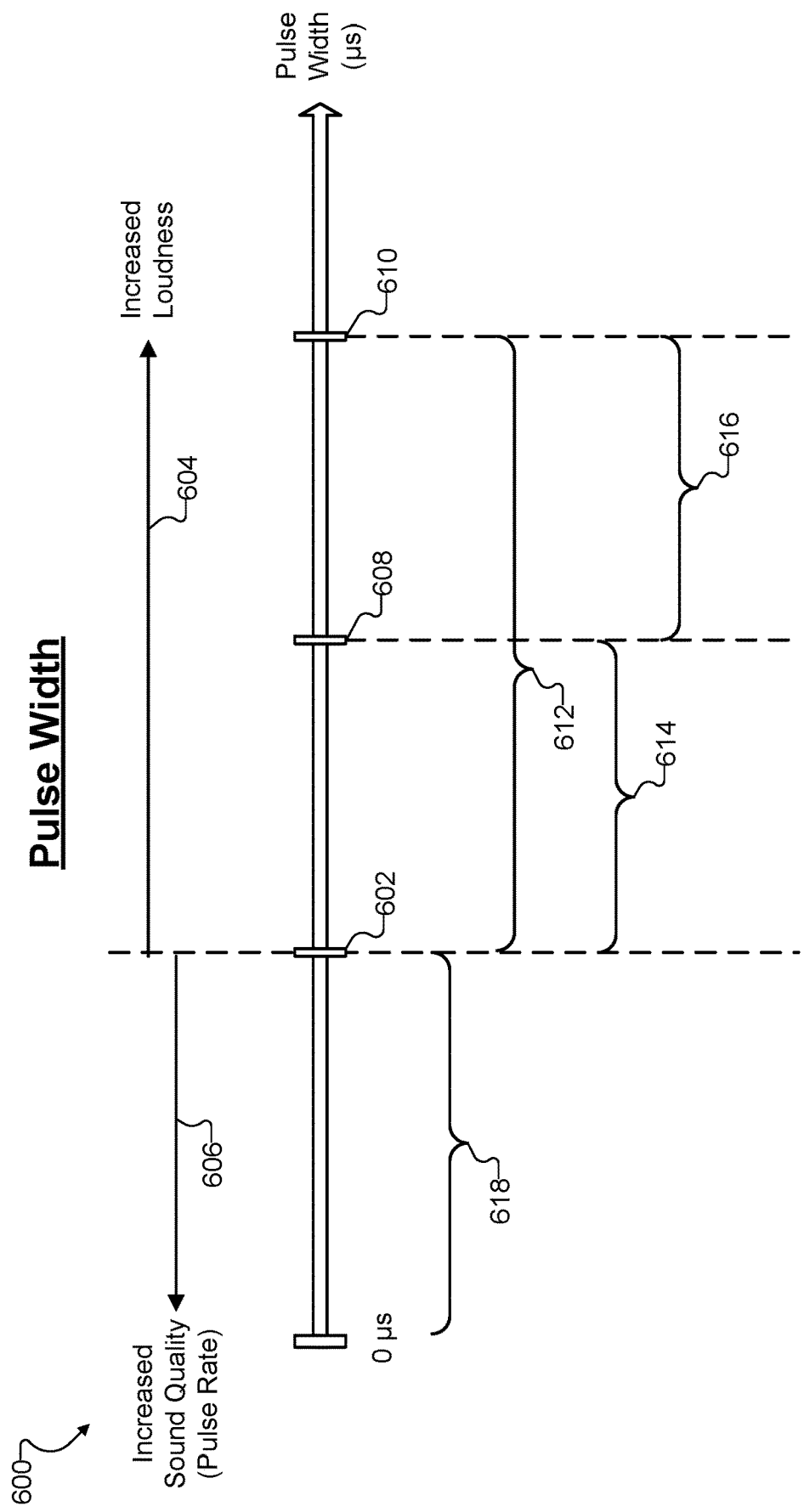
FIG. 6 illustrates various exemplary aspects of how the apparatus of FIG. 3 may set a pulse width stimulation parameter based on an electrode impedance measurement according to principles described herein.

FIG. 6 illustrates various exemplary aspects of how apparatus 300 may set a pulse width stimulation parameter based on an electrode impedance measurement. As shown in FIG. 6, a stimulation parameter to be adjusted by apparatus 300 may be a pulse width 600 associated with stimulation pulses applied to the patient by way of the electrode during a normal operation of cochlear implant system 100. Pulse width 600 is illustrated as a linear continuum of potential pulse width values greater than or equal to 0 μs. As shown, a present value 602 may represent a value of pulse rate 600 that may be set prior to any adjustment by apparatus 300. An arrow 604 illustrates that, as pulse rate 600 is adjusted in a positive direction (i.e., as pulse rate 600 is increased by moving to the right), the patient may perceive increased loudness. At the same time, an arrow 606 illustrates that, as pulse rate 600 is adjusted in a negative direction (i.e., as pulse rate 600 is decreased by moving to the left), the patient may perceive increased sound quality (e.g., due to an increased pulse rate). Accordingly, as described above, arrows 604 and 606 collectively illustrate a tradeoff between loudness and sound quality that may be accounted for as pulse rate 600 is adjusted.

As mentioned above, one way that such a tradeoff may be effectively accounted for is by using adjustment constraints. Accordingly, two additional values 608 and 610 of pulse rate 600 that are both greater than present value 602 (i.e., representing longer pulse width values) are shown. In some examples, an adjustment constraint may be determined and set by a medical professional administering care of the patient as a maximum pulse width. For example, value 610 of pulse rate 600 may represent a maximum pulse width value of such an adjustment constraint. As such, apparatus 300 may automatically adjust pulse rate 600 by automatically increasing pulse width 600 to a longer pulse width that is still below the maximum pulse width represented by value 610 (e.g., that is any value up to and including the maximum pulse width of value 610). In other words, apparatus 300 may adjust pulse rate 600 from present value 602 to any value within a range 612 of pulse width values that are greater than present value 602 and less than value 610 of the adjustment constraint.

In some examples, apparatus 300 may perform this type of adjustment automatically (e.g., without further user involvement, permission, direction, etc.). Because the medical professional may have determined that the corresponding decrease in sound quality will not be problematic for the patient when pulse width 600 has a value below value 610, for example, apparatus 300 may freely adjust pulse width 600 from value 602 to any value within range 612 that will result in the perceived loudness reaching a desirable level (e.g., based on a change to the electrode impedance).

In the same or other examples, apparatus 300 may perform an automatic adjustment only up to a value such as value 608 (i.e., up to any value within a range 614), and may require user input to go to a value greater than value 608 (i.e., to any value within a range 616). For example, while value 610 may be associated with an absolute adjustment constraint (i.e., a constraint that the system is not to surpass with or without user input), value 608 may be associated with a tentative adjustment constraint (i.e., a constraint that the system is not to surpass automatically, but may surpass based on user input).

Accordingly, in one example, apparatus 300 may identify an adjustment constraint that is an absolute stimulation parameter adjustment constraint. For instance, the absolute adjustment constraint may be associated with value 610. Apparatus 300 may further identify an additional adjustment constraint that is a tentative stimulation parameter adjustment constraint associated with a value between present value 602 of pulse width 600 and value 610 associated with the absolute stimulation parameter adjustment constraint. For instance, the tentative adjustment constraint may be associated with value 608. Having identified both the absolute and the tentative adjustment constraints, apparatus 300 may automatically adjust pulse width 600, based on the impedance of the electrode, to value 608 associated with the tentative stimulation parameter adjustment constraint. Apparatus 300 may then provide an alert associated with adjusting the stimulation parameter to a value beyond value 608 (e.g., a value within range 616), receive user input manually provided by the patient (or a caretaker) to cochlear implant system 100 in response to the alert that the stimulation parameter is to be adjusted to the value beyond value 608, and adjust (e.g., based on the user input) the stimulation parameter to the value beyond value 608. However, the value beyond value 608 may not go beyond value 610 associated with the absolute stimulation parameter adjustment constraint. In other words, the value to which apparatus 300 adjusts pulse width 600 based on the user input may be within range 616.

In some examples, it may be undesirable to adjust stimulation parameters such as pulse width 600 immediately after detecting a change in electrode impedance and/or based on relatively small changes in electrode impedance. Accordingly, adjustment constraints associated with a particular stimulation parameter such as pulse width 600 may be set to define values and/or ranges designated as meriting automatic and/or non-automatic parameter adjustments. For instance, rather than being associated with a tentative adjustment constraint, value 608 may be associated, in certain implementations, with a minimum adjustment that apparatus 300 is configured to make. For example, if the electrode impedance is determined to have changed, but is changing slowly or by small amounts such that a desired increase in loudness level would call for an adjustment of present value 602 to a value within range 614, apparatus 300 may not make this adjustment, or at least may not do so immediately. Rather, apparatus 300 may wait until the electrode impedance has stabilized for a certain period of time and/or has changed such that the desired increase in loudness level would call for an adjustment of present value 602 to a value within range 616. In this way, the stimulation parameters and resulting perceived loudness level may be kept stable and predictable for the patient until a significant electrode impedance change is detected, rather than the stimulation parameters being constantly readjusted in a potentially disorienting way as normal electrode impedance fluctuations occur and/or in response to small inconsistencies between electrode impedance measurements caused by imperfect measurements or the like.

While the focus of FIG. 6 and the description related thereto has related to increasing loudness due to a detected increase in electrode impedance, it will be understood that electrode impedance may also be determined to have changed in such a way that it is desirable to decrease present value 602 to a value within a range 618. In these examples, similar absolute and/or tentative adjustment constraints may be used as described above, except that these constraints may represent lower bounds rather than upper bounds. Additionally, as mentioned above, some changes in electrode impedance may be temporary by nature (e.g., such as those changes brought on by illness, etc.). As such, after a period of time when pulse width 600 has been adjusted from present value 602 to a value within range 612, it may be determined, based on a reverting of the electrode impedance back to a lower value, that pulse width 600 is to be adjusted downward (e.g., back to value 602 or to another suitable value).

Figure 7:
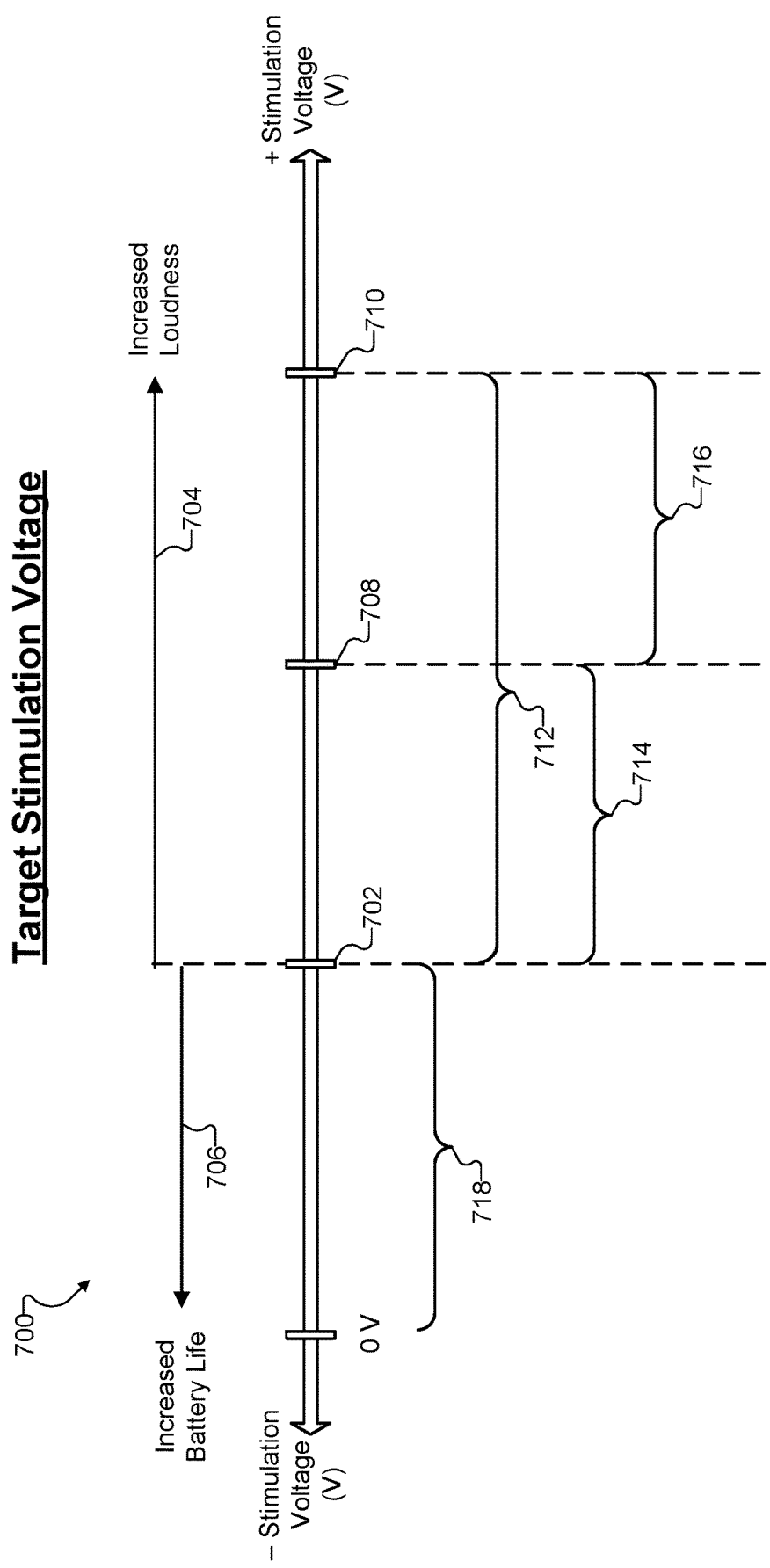
FIG. 7 illustrates various exemplary aspects of how the apparatus of FIG. 3 may set a target stimulation voltage stimulation parameter based on an electrode impedance measurement according to principles described herein.

FIG. 7 illustrates various exemplary aspects of how apparatus 300 may set a target stimulation voltage stimulation parameter based on an electrode impedance measurement. As shown in FIG. 7, a stimulation parameter to be adjusted by apparatus 300 may be a target stimulation voltage 700 at which stimulation pulses are applied to the patient by way of the electrode during normal operation of cochlear implant system 100. As with pulse width 600, target stimulation voltage 700 is illustrated as a linear continuum of potential stimulation voltages from lower stimulation voltages at the left to higher stimulation voltages at the right. As shown, a present value 702 may represent a value of target stimulation voltage 700 that may be set prior to any adjustment by apparatus 300. An arrow 704 illustrates that, as target stimulation voltage 700 is adjusted in a positive direction (i.e., as target stimulation voltage 700 is increased by moving to the right), the patient may perceive increased loudness. At the same time, an arrow 706 illustrates that, as target stimulation voltage 700 is adjusted in a negative direction (i.e., as target stimulation voltage 700 is decreased by moving to the left), the battery life of cochlear implant system 100 may improve. Accordingly, as described above, arrows 704 and 706 collectively illustrate a tradeoff between loudness and battery life that may be accounted for as target stimulation voltage 700 is adjusted.

As described above in relation to pulse width 600, one way that such a tradeoff may be effectively accounted for is by using adjustment constraints. Accordingly, corresponding values 708 and 710 are shown to represent larger target stimulation voltage values than present value 702 and are analogous to values 608 and 610 in FIG. 6. Values 708 and 710 may analogously represent tentative and absolute adjustment constraints similar to those described above in relation to pulse width 600, and/or to other types of adjustment constraints described herein. Specifically, value 710 may be associated with an adjustment constraint determined and set by the medical professional and may be a maximum target stimulation voltage. As such, apparatus 300 may automatically adjust target stimulation voltage 700 by automatically increasing target stimulation voltage 700 to a larger target stimulation voltage that is still below the maximum target stimulation voltage of value 710. For instance, in certain implementations, apparatus 300 may perform adjustments up to value 708 automatically and adjustments beyond value 708 up to value 710 based on user input. As such, ranges 712, 714, 716, and 718 may be analogous to ranges 612, 614, 616, and 618, respectively.

Figure 8:
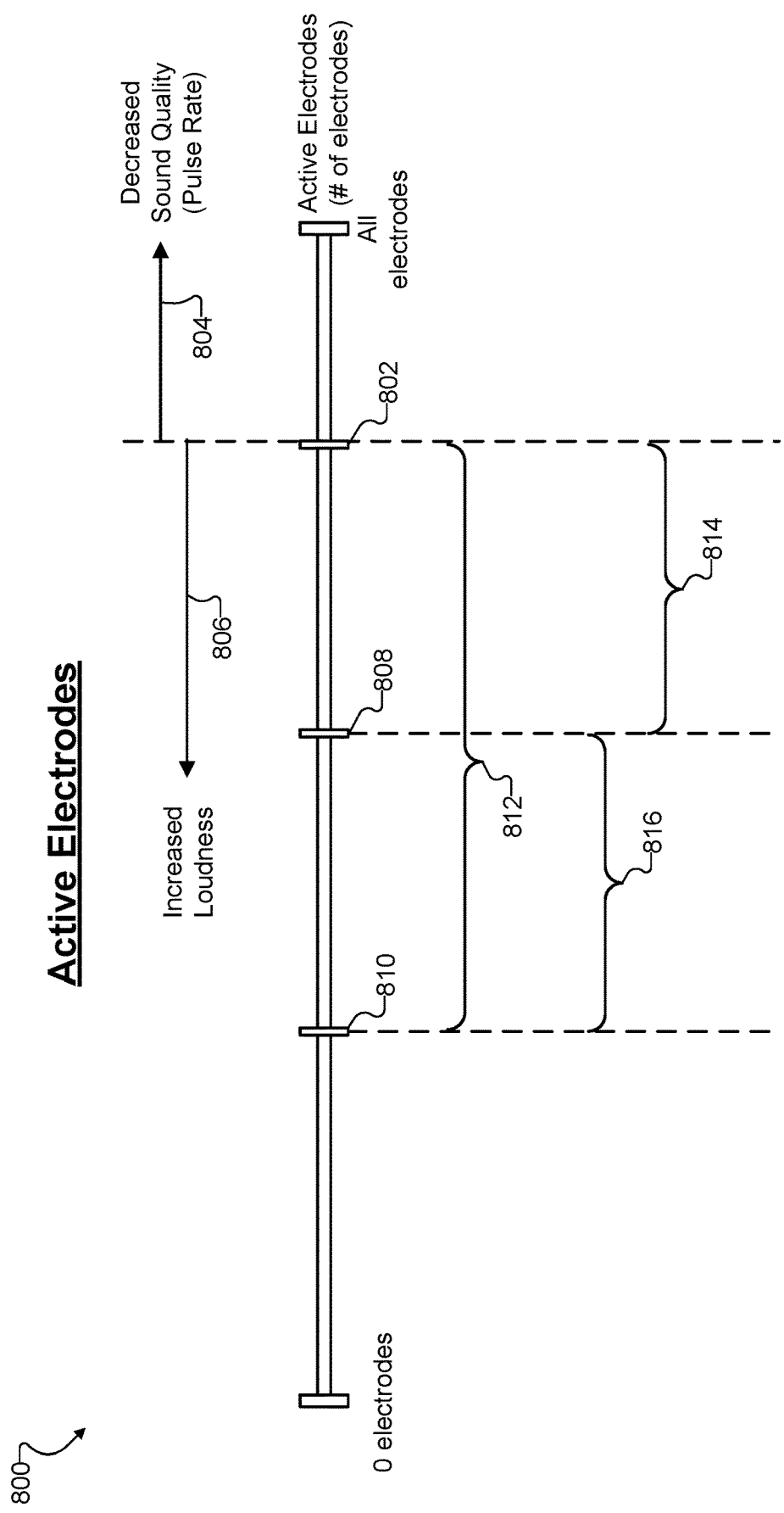
FIG. 8 illustrates various exemplary aspects of how the apparatus of FIG. 3 may set an active electrode stimulation parameter based on an electrode impedance measurement according to principles described herein.

FIG. 8 illustrates various exemplary aspects of how apparatus 300 may set an active electrode stimulation parameter based on an electrode impedance measurement. As shown in FIG. 8, a stimulation parameter to be adjusted by apparatus 300 may be a number of active electrodes 800 that are active in applying stimulation pulses to the patient by way of the electrode during a normal operation of cochlear implant system 100. As with pulse width 600 and target stimulation voltage 700, number of active electrodes 800 is illustrated as a linear continuum of potential numbers of active electrodes from none of the electrodes at the left to all of the electrodes at the right. However, unlike with pulse width 600 and target stimulation voltage 700, it will be understood that the number of active electrodes 800 may be limited to integers (e.g., integers between 0 and 16 in an exemplary 16-electrode implementation), rather than to arbitrary real numbers anywhere on the number line.

As shown, a present value 802 may represent a present number of active electrodes that may be in use prior to any adjustment by apparatus 300. An arrow 804 illustrates that, as the number of active electrodes 800 is adjusted in a positive direction (i.e., as more active electrodes are activated for use by moving the value to the right), the patient may perceive decreased sound quality at least with respect to the pulse rate. It will be understood that in certain respects, a larger number of active electrodes may provide a fuller and more accurate reproduction of sound than a smaller number of active electrodes because more frequency ranges may be stimulated using the greater number of active electrodes. However, for a given pulse width, a larger number of active electrodes will also result in a smaller pulse rate than will a smaller number of active electrodes. Thus, for example, if pulse width 600 has already been increased to a value that verges on compromising the sound quality due to a relatively low pulse rate, increasing the number of active electrodes 800 may actually cause the sound quality to be degraded in a perceivable way. At the same time, an arrow 806 illustrates that, as the number of active electrodes 800 is adjusted in a negative direction (i.e., as the number decreases by moving to the left), the loudness level perceived by the patient may increase, or at least may make it possible to further increase the loudness level without the same negative consequences by, for example, further adjusting pulse width 600 and/or target stimulation voltage 700. Accordingly, as described above, arrows 804 and 806 collectively illustrate yet another tradeoff that may be accounted for as the number of active electrodes 800 is adjusted.

As described above in relation to pulse width 600 and target stimulation voltage 700, one way that such a tradeoff may be effectively accounted for is by using adjustment constraints. Accordingly, corresponding values 808 and 810 are shown that may be analogous to values 608 and 610, respectively, in FIG. 6 and to values 708 and 710, respectively, in FIG. 7. However, because increased loudness levels are achieved by smaller numbers of active electrodes for this particular stimulation parameter, values 808 and 810 are shown to be smaller than present value 802, rather than larger as were the analogous values in FIGS. 6 and 7. As such, values 808 and 810 may represent tentative and absolute adjustment constraints similar to those described above in relation to pulse width 600 and target stimulation voltage 700, and/or to other types of constraints described herein. However, rather than being associated with upper bounds as were the adjustment constraints associated with pulse width 600 and target stimulation voltage 700, it will be understood that the adjustment constraints illustrated by values 808 and 810 are associated with a lower bound of electrodes in active use.

As such, value 810 may be associated with an adjustment constraint determined and set by the medical professional and may be a minimum number of active electrodes. As such, apparatus 300 may automatically adjust the number of active electrodes 800 by automatically deactivating one or more electrodes to get down to a smaller number of active electrodes that is still above (or equal to) the minimum number of active electrodes represented by value 810. For instance, in certain implementations, apparatus 300 may perform adjustments down to value 808 automatically and adjustments beyond value 808 down to value 810 based on user input. As such, ranges 812, 814, and 816 may likewise be analogous to ranges 612, 614, and 616, respectively, in FIG. 6 and/or to ranges 712, 714, and 716, respectively, in FIG. 7.

The exemplary adjustment constraints described in relation to FIGS. 6, 7, and 8 have all been described as being associated with absolute or tentative values constraining the degree to which apparatus 300 may adjust different stimulation parameters (e.g., automatically or with user input). As mentioned above, however, other types of adjustment constraints may also be used in certain implementations. For example, an adjustment constraint may be associated with a predetermined adjustment timeline set by the patient, a caretaker of the patient, and/or a medical professional facilitating care of the patient with respect to the cochlear implant system. For example, the predetermined adjustment timeline may specify a plurality of automatic stepwise adjustments associated with a stimulation parameter (e.g., any of the stimulation parameters 600, 700, or 800, or another suitable stimulation parameter) to facilitate a gradual adjustment of the stimulation parameter from an initial value to a target value. The predetermined adjustment timeline may additionally or alternatively specify designated time intervals to be inserted between the automatic stepwise adjustments in the plurality of automatic stepwise adjustments associated with the stimulation parameter.

To illustrate, FIG. 9 shows an exemplary predetermined adjustment timeline for setting cochlear implant system stimulation parameters based on electrode impedance measurements. More specifically, FIG. 9 illustrates a stimulation parameter 900 that may represent any of the stimulation parameters described herein (e.g., pulse width 600, target stimulation voltage 700, number of active electrodes 800, etc.), as well as a predetermined adjustment timeline 902 ("timeline 902") that illustrates how the value of the stimulation parameter is gradually increased in a stepwise fashion as time moves to the right from an initial starting time "T=0". As shown, at the initial time, stimulation parameter 900 may be set to an initial value 904. Based on the determined electrode impedance and in accordance with one or more adjustment constraints, apparatus 300 may gradually increase stimulation parameter 900 from initial value 904 to a target value 906 by way of a plurality of intermediate values 908 (e.g., intermediate values 908-1 through 908-4) to which stimulation parameter 900 is adjusted in a stepwise fashion at a plurality of times 910 (e.g., times 910-1 through 910-4) on timeline 902.

Intermediate values 908 and times 910 may be distributed in any manner as may serve a particular implementation. For example, values 908 may be evenly distributed between initial value 904 and target value 906 or may be distributed in another way (e.g., asymptotically, etc.) or in a combination of ways. For instance, as shown, the first several intermediate values 908 may be evenly spaced, while later intermediate values 908 may have a different spacing. Times 910 may similarly be distributed along timeline 902 in any suitable manner. For instance, times 910 may be distributed evenly (e.g., once an hour, one a day), unevenly at specific times, or may be associated with events rather than specific times of day (e.g., events such as powering on the cochlear implant system for the first time of the day).

Adjustment constraints may be employed to constrain and designate any aspect of the adjustment from initial value 904 to target value 906. For example, an adjustment constraint may define both a total adjustment range 912 that stimulation parameter 900 is to be adjusted, as well as details about an individual step range 914 for each stepwise adjustment of stimulation parameter 900. While FIG. 9 illustrates stepwise adjustments that may be made for increasing stimulation parameter 900, it will be understood that similar principles may be applied for decreasing stimulation parameter 900 (e.g., when the electrode impedance is detected to return to an initial value, in situations where stimulation parameter 900 is lowered rather than raised to account for the detected electrode impedance, etc.).

As mentioned above, in some examples, apparatus 300 may generate an alert that is associated with the electrode impedance and is adapted for presentation to a user associated with cochlear implant system 100 (e.g., the patient, a caretaker of the patient, a clinician who works with the patient, etc.). For instance, apparatus 300 may generate the alert in response to the determination of the impedance of the electrode instead of, or in addition to, automatically adjusting a stimulation parameter associated with cochlear implant system 100.

The alert associated with the electrode impedance and generated by apparatus 300 may indicate, represent, or be associated with any data, notification, status, or the like as may serve a particular implementation. For example, apparatus 300 may generate the alert associated with the impedance of the electrode based on the automatic adjustment of the stimulation parameter. As such, the alert associated with the impedance of the electrode may indicate details about adjustments that have been made. For example, the alert may include a notification that one or more particular stimulation parameters (e.g., stimulation parameters 600, 700, or 800) has been adjusted from a particular value to a new value. As another example, in implementations in which the automatic adjustment is performed by switching sound processor 104 from operating in accordance with a first sound processing program to operating in accordance with a second sound processing program, the alert may indicate one or both sound processing programs and indicate that the sound processor has switched from operating in accordance with the first sound processing program to operating in accordance with the second sound processing program.

Additionally or alternatively, alerts generated by apparatus 300 and adapted for presentation to the user may indicate data, notifications, statuses, etc., that are indirectly related or unrelated to stimulation parameters adjustments and/or sound processing program changes. For instance, as described above, apparatus 300 may determine (e.g., based on the determined impedance of the electrode, subsequent to a stimulation parameter adjustment, etc.) that cochlear implant system 100 is operating outside of the normal compliance mode. Thus, as a result of this determination, the alert associated with the impedance of the electrode may indicate that the cochlear implant system is operating outside of the normal compliance mode. In this way, the user associated with the cochlear implant system may be made aware that the patient may not be receiving stimulation at proper levels due to the cochlear implant system operating outside of the normal compliance mode, and the user may take corrective actions (e.g., arrange for the patient to meet with a clinician to troubleshoot the problem).

Figure 10B:
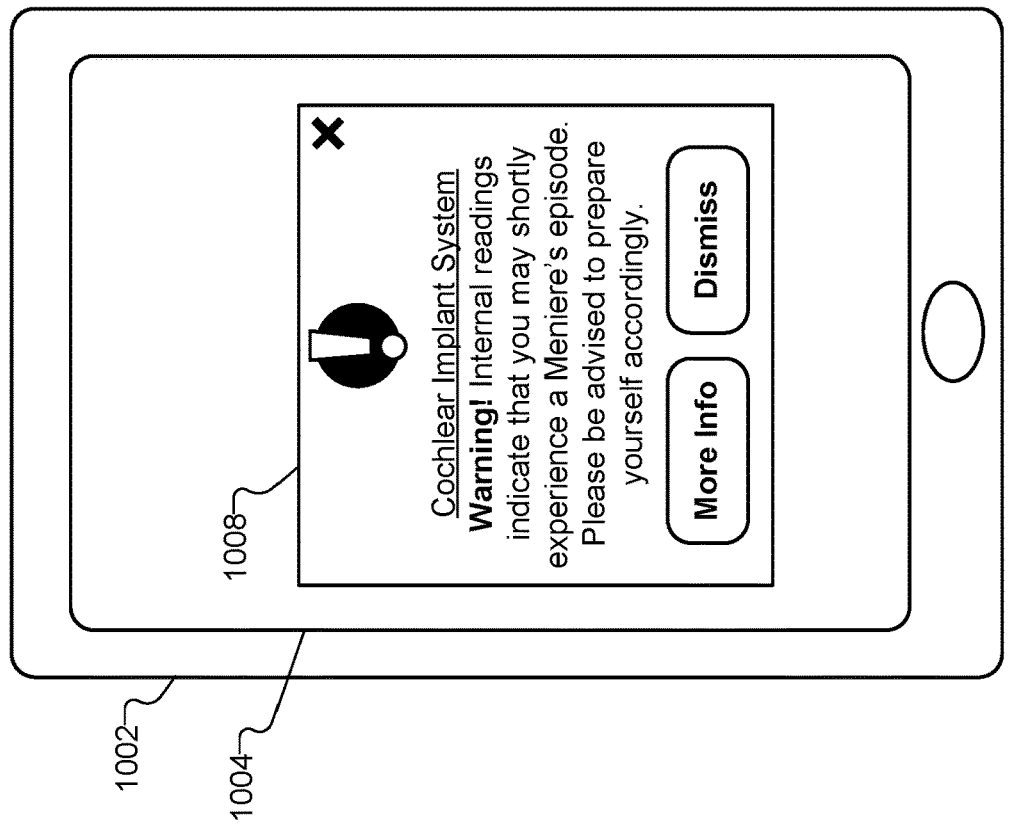
FIGS. 10A and 10B illustrate exemplary alerts adapted for presentation to a user associated with a cochlear implant system according to principles described herein.
Figure 10A:
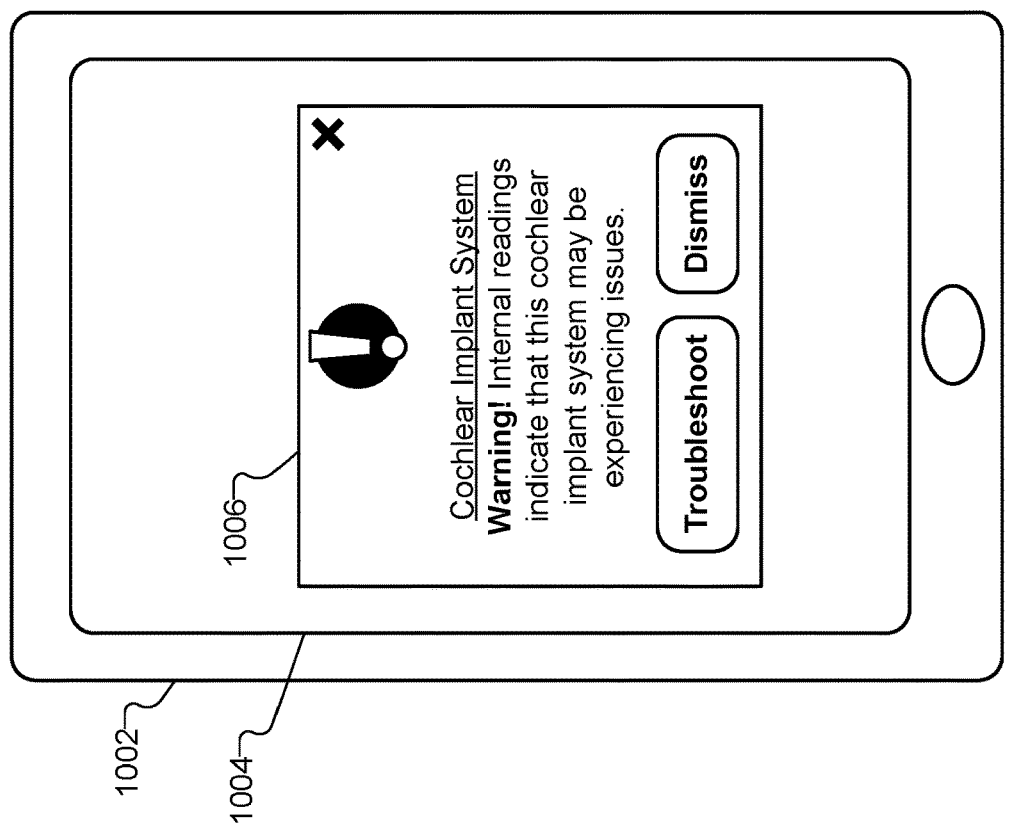

To illustrate, FIG. 10A shows an exemplary alert adapted for presentation to a user associated with cochlear implant system 100. Specifically, as shown in FIG. 10A, a mobile computing device 1002 may present, on a display screen 1004 of mobile computing device 1002, an alert 1006. As with other mobile computing devices described herein, mobile computing device 1002 may be communicatively coupled with cochlear implant system 100 and may implement and/or be communicatively coupled with an implementation of apparatus 300. As shown, alert 1006 may be displayed as a pop-up notification on display screen 1004. Additionally or alternatively, alert 1006 may be presented on display screen 1004 in a different manner (e.g., using another suitable type of alert or notification), may involve sound, may involve haptic feedback, and/or may otherwise be presented in any way that may serve a particular implementation. Regardless of how alert 1006 is presented, alert 1006 may be configured to indicate to the user that cochlear implant system 100 is operating outside of the normal compliance mode. Additionally, as shown, alert 1006 may provide one or more selectable options (e.g., troubleshooting options, etc.) to assist the user in readjusting the stimulation parameters to no longer cause the system to operate outside of the normal compliance mode (e.g., by loading a different sound processing program), to assist the user in contacting a clinician to setup an appointment, or to otherwise provide troubleshooting guidance for fixing the compliance issue or other information.

In certain examples, the user associated with cochlear implant system 100 to whom the alert associated with the impedance is adapted for presentation may be a person other than the patient using the cochlear implant system. For example, the user receiving the alert may be a caretaker (e.g., a parent, nurse, etc.) of the patient. It may be difficult for such a person (i.e., a person who is not the patient and is thus not directly experiencing the out-of-compliance issues of the cochlear implant system) to assess how serious a problem is (e.g., how degraded the listening experience of the patient has become) based only on a description included in a textual alert message. As a result, in certain implementations, the alert associated with the impedance may include an additional user interface option (e.g., a button or the like) allowing the user to elect to listen to an audio simulation that simulates a hearing experience provided to the patient by the cochlear implant system while the cochlear implant system is operating outside the normal compliance mode. In other words, a person associated with the patient such as a parent or other caretaker may be presented with an audio presentation that simulates the amount of quality degradation that the patient is experiencing due to the cochlear implant system's operation outside of the normal compliance mode. In this way, the person may more easily make important subjective decisions about how serious the compliance problem is, how quickly it needs to be resolved, and so forth.

In other examples, as further described above, apparatus 300 may determine, based on the determined electrode impedance, that the patient is experiencing or is about to experience an altered hearing episode such as a Meniere's episode, a middle ear effusion episode (i.e., an ear infection), a common cold episode, or the like. Accordingly, as another example of an alert that may be presented to a user associated with the cochlear implant system, the alert may include an indication or notification related to the altered hearing episode. While this type of alert may be helpful information for a person other than the patient to know, this type of alert may be particularly relevant for the patient himself or herself to know, since the alert may provide important safety information or the like.

As one particular example, the user to whom the alert associated with the impedance is adapted for presentation may be the patient using the cochlear implant system and apparatus 300 may determine (e.g., based on the determined impedance of the electrode) that the patient is likely to experience a Meniere's episode. The alert associated with the impedance of the electrode may indicate that the patient is likely to experience the Meniere's episode. This may allow the patient to take measures to mitigate any danger or unwanted circumstances that could occur if the Meniere's episode happened by surprise. For example, if the patient is driving a car, the patient may pull over upon receiving the alert that he or she is likely to soon experience a Meniere's episode (e.g., with its accompanying vertigo, tinnitus, etc., which could make driving dangerous). In other examples, the patient may sit down, drink a cup of coffee, eat a salty snack, or take another measure to prepare for and/or help mitigate the effects of the Meniere's episode. In many examples, the alert may be provided to the patient before the Meniere's episode actually begins, or before the worst of the symptoms are experienced, to allow the patient to take these or other actions and avoid some of the negative consequences that otherwise might occur.

To illustrate, FIG. 10B shows another exemplary alert adapted for presentation to the patient associated with cochlear implant system 100. Specifically, as shown in FIG. 10B, mobile computing device 1002 may present an alert 1008 on display screen 1004 in the same manner as described above for alert 1006 and/or in any other suitable manner described herein or as may serve a particular implementation. Regardless of how alert 1008 is presented, alert 1008 may be configured to indicate to the patient that, based on the determined electrode impedance, the patient is likely to experience a Meniere's episode in the relatively near future, and may advise the patient to prepare accordingly. Apparatus 300 may further provide one or more selectable options to assist the user in acquiring more information about how the determination regarding the impending Meniere's episode was made, what types of things the patient is advised to do in preparation for the Meniere's episode, and so forth.

Additionally or alternatively, other determinations related to cochlear implant system 100 may similarly be made based on detected electrode impedances and these may be similarly brought to the user's attention by way of suitable alerts similar to those illustrated in FIGS. 10A and 10B. For instance, as described above, an array of electrodes (e.g., electrodes 112 of cochlear implant system 100, electrodes 512 of cochlear implant system 500, etc.) disposed on a lead (e.g., lead 110 or 510, respectively) may be inserted into a cochlea of the patient to apply stimulation to various stimulation sites within the cochlea such as described above in relation to FIG. 2. In some examples, however, the lead inserted into the cochlear (including one or more electrodes disposed on the lead) may inadvertently become displaced from a proper location within the cochlea where the lead is implanted. For example, various factors may cause the lead to gradually recede from (e.g., back out of) the cochlea. Eventually, the lead may recede enough that one or more of the basal electrodes may no longer be in contact with the nerve tissue of the cochlea, causing the one or more basal electrodes to exhibit significant changes in electrode impedance.

As a result, in certain examples, apparatus 300 may determine (e.g., based on the determined impedance of a basal electrode that has receded from the cochlea) that the electrode has become displaced from a predetermined position within the patient (e.g., has receded or backed out of the cochlea). As such, the alert associated with the impedance of the electrode may indicate that the electrode has become displaced from the predetermined position within the patient, allowing the user (e.g., the patient, a caretaker of the patient, etc.) to arrange for the patient to get appropriate medical attention to have the lead reinserted and properly set into the cochlea.

Regardless of what type of alert is sent and what the alert indicates, alerts provided to users associated with the cochlear implant system may be adapted for presentation to the users according to who the intended user is, what the user knows, and the like. Accordingly, alerts provided for the benefit of patients directly may include different types of details than alerts provided for users such as caretakers of the patient, or clinicians working with the patient. For example, alerts adapted for presentation to parents of a three-year-old pediatric patient may be adapted to carefully present notifications related to the cochlear implant system used by the pediatric patient without causing the parents to worry more than the situations merits. For instance, if a cochlear implant system is out of compliance, the patient may be fine with subpar hearing for a few days (i.e., it may not be an emergency), so a high priority alert may be avoided for parents that may be prone to worry. At the same time, it may be important that such problems are fixed before too long (e.g., to avoid negative effects on the patient's long-term development). Thus, alerts may become increasingly serious after a few days if the problem has not been remedied. Similarly, alerts that are adapted for presentation to a parent may include more or different information than alerts adapted for presentation to a child, just as alerts that are adapted for presentation to a clinician may include more or different information than alerts that are adapted for presentation to the parent or to an adult patient.

Figure 11:
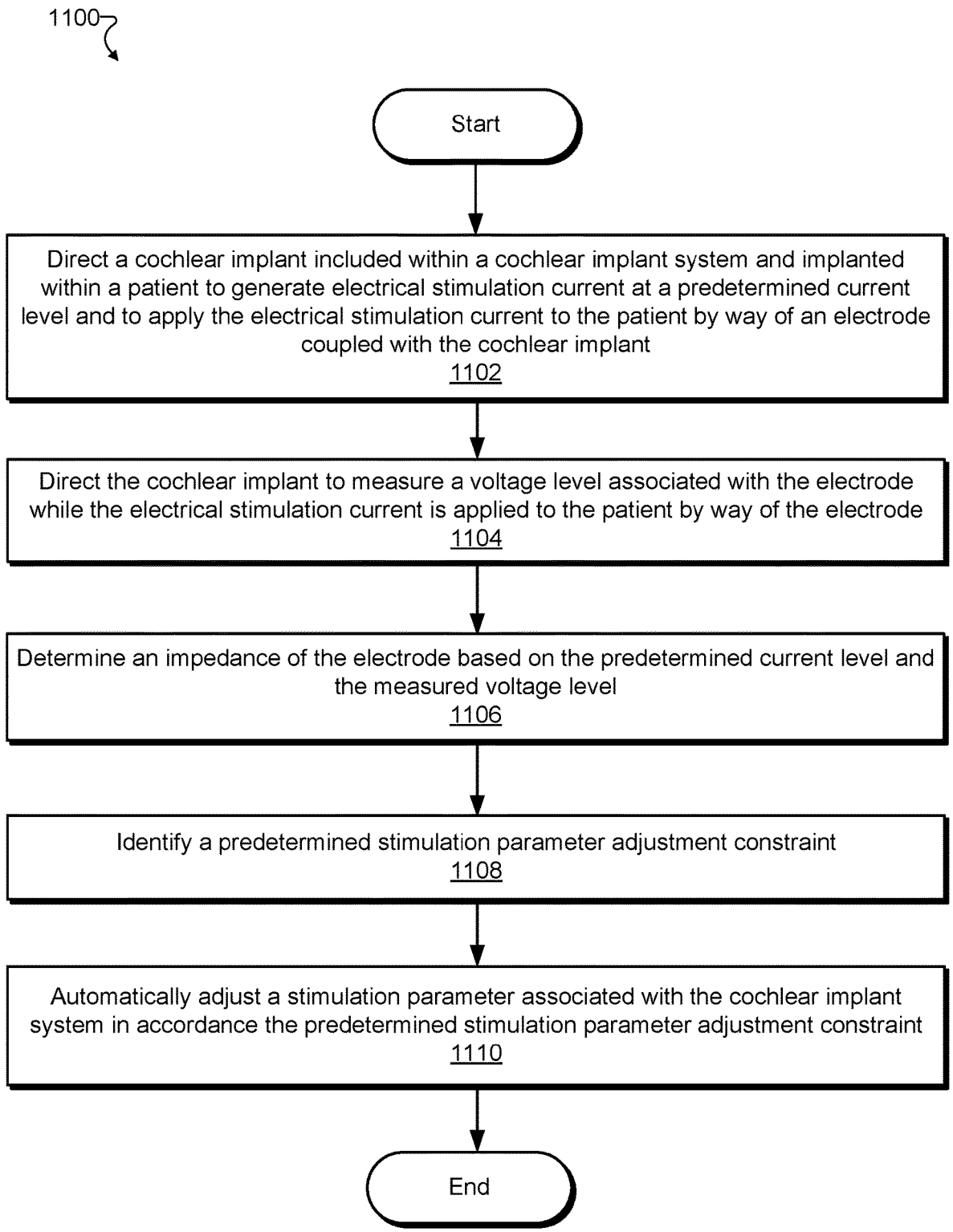
FIG. 11 illustrates an exemplary method for setting cochlear implant system stimulation parameters based on electrode impedance measurements according to principles described herein.

FIG. 11 illustrates an exemplary method 1100 for setting cochlear implant system stimulation parameters based on electrode impedance measurements. While FIG. 11 illustrates exemplary operations according to one embodiment, other embodiments may omit, add to, reorder, and/or modify any of the operations shown in FIG. 11. One or more of the operations shown in FIG. 11 may be performed by an apparatus for setting cochlear implant system stimulation parameters based on electrode impedance measurements such as apparatus 300 and/or any implementation thereof.

In operation 1102, an apparatus associated with a cochlear implant system used by a patient may direct a cochlear implant to generate electrical stimulation current at a predetermined current level. The cochlear implant may be included within the cochlear implant system and may be implanted within the patient. Along with generating the electrical stimulation current in operation 1102, the apparatus may direct the cochlear implant to apply the electrical stimulation current to the patient by way of an electrode coupled with the cochlear implant. Operation 1102 may be performed in any of the ways described herein.

In operation 1104, the apparatus may direct the cochlear implant to measure a voltage level associated with the electrode while the electrical stimulation current is applied to the patient by way of the electrode. Operation 1104 may be performed in any of the ways described herein.

In operation 1106, the apparatus may determine an impedance of the electrode. For example, the apparatus may determine the impedance of the electrode based on the predetermined current level applied in operation 1102 and the voltage level measured in operation 1104. Operation 1106 may be performed in any of the ways described herein.

In operation 1108, the apparatus may identify an adjustment constraint. Operation 1108 may be performed in any of the ways described herein.

In operation 1110, the apparatus may automatically adjust a stimulation parameter associated with the cochlear implant system. For example, the apparatus may automatically adjust the stimulation parameter based on the impedance of the electrode determined in operation 1106 and in accordance the adjustment constraint identified in operation 1108. Operation 1110 may be performed in any of the ways described herein.

Many of the figures shown and examples described above have related specifically to apparatuses and methods for setting cochlear implant system stimulation parameters based on electrode impedance measurements. However, as mentioned previously, it will be understood that apparatuses and methods described herein may be useful for acquiring and using cochlear implant electrode impedance measurement in a variety of ways in addition to setting cochlear implant system stimulation parameters.

Figure 12:
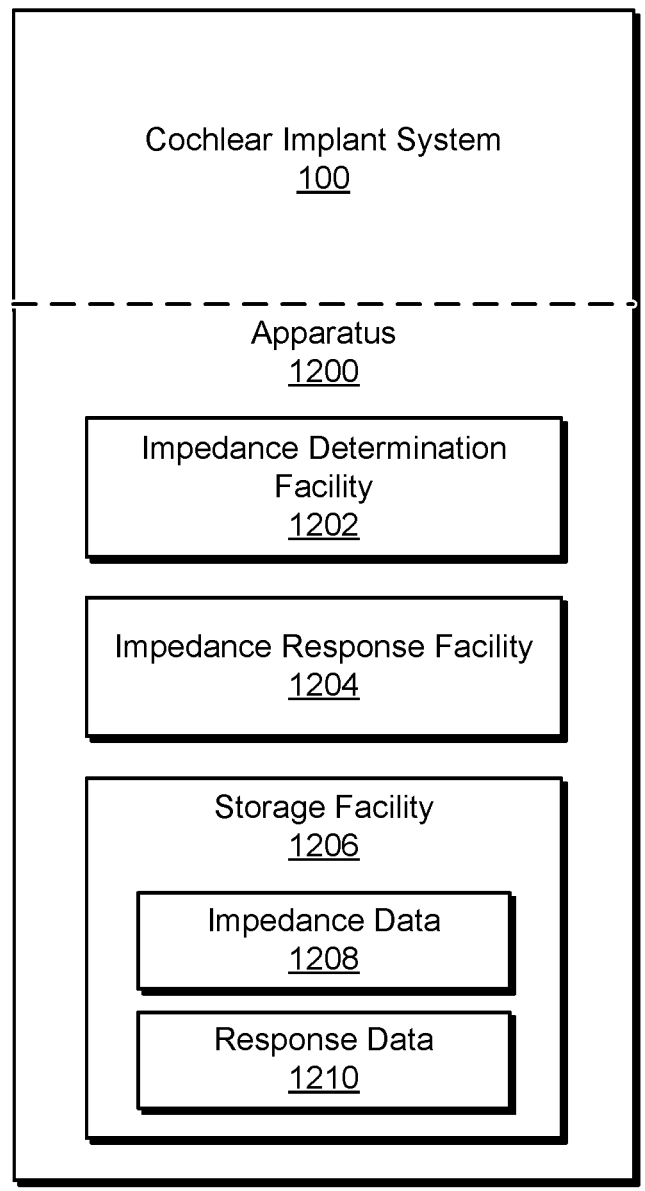
FIG. 12 illustrates an exemplary apparatus for acquiring and using cochlear implant electrode impedance measurements according to principles described herein.

For example, FIG. 12 illustrates an exemplary apparatus 1200 for acquiring and using cochlear implant electrode impedance measurements in a variety of ways (e.g., including by setting cochlear implant system stimulation parameters as specifically described above in relation to apparatus 300, as well as by performing other operations as will be described below).

Similar to apparatus 300, apparatus 1200 may be associated with a cochlear implant system such as cochlear implant system 100 in various ways and may be implemented by various components that are either part of the cochlear implant system or separate from, but communicatively coupled with, the cochlear implant system. Thus, for example, apparatus 1200 may be implemented by sound processor 104 within cochlear implant system 100 (e.g., or by sound processor 506 within cochlear implant system 500 or another suitable sound processor in other implementations), by cochlear implant 108 within cochlear implant system 100 (e.g., or by integrated cochlear implant 504 within cochlear implant system 500 or another suitable cochlear implant in other implementations), by mobile computing device 402 communicatively coupled to cochlear implant system 100, and/or by any other suitable apparatus associated with cochlear implant system 100 as may serve a particular implementation.

As shown, apparatus 1200 may include, without limitation, an impedance determination facility 1202, an impedance response facility 1204, and a storage facility 1206 selectively and communicatively coupled to one another. It will be recognized that although facilities 1202 through 1206 are shown to be separate facilities in FIG. 12, facilities 1202 through 1206 may be combined into fewer facilities, such as into a single facility, or divided into more facilities as may serve a particular implementation. Each of facilities 1202 through 1206 will now be described in more detail.

Similar to impedance determination facility 302 described above, impedance determination facility 1202 may include one or more physical computing components that are associated with cochlear implant system 100. Using the one or more physical computing components, impedance determination facility 1202 may perform any of various operations to determine an electrode impedance for at least one electrode 112 included in cochlear implant system 100. For example, impedance determination facility 1202 may direct cochlear implant 108 implanted within the patient to generate electrical stimulation current at a predetermined current level, and to apply the electrical stimulation current to the patient by way of an electrode 112 coupled with cochlear implant 108. Impedance determination facility 1202 may further direct cochlear implant 108 to measure a voltage level associated with the electrode 112 while the electrical stimulation current is applied to the patient by way of the electrode 112. Then, based on the predetermined current level and the measured voltage level, impedance determination facility 1202 may determine an impedance of the electrode 112 using techniques described herein.

Once the impedance of the electrode 112 has been determined by impedance determination facility 1202, apparatus 1200 may perform, direct, or facilitate one or more additional operations based on the determined electrode impedance and/or in response to the determination of the electrode impedance. Such operations may be referred to herein as "response operations" or "impedance response operations" since they are performed as responses to the determination of the electrode impedance.

To this end, similar to parameter adjustment facility 304, impedance response facility 1204 may include one or more physical computing components that perform, direct, facilitate, or otherwise provide impedance response operations subsequent to a determination of an electrode impedance by impedance determination facility 1202. Impedance response facility 1204 may perform any impedance response operations described herein or as may serve a particular implementation. Certain examples of impedance response operations will be mentioned now and described in more detail below.

For instance, as one example of an impedance response operation, impedance response facility 1204 may set cochlear implant system stimulation parameters in any of the ways described herein (e.g., by automatically adjusting stimulation parameters in accordance with adjustment constraints, by automatically directing a sound processor included within the cochlear implant system to switch from operating in accordance with a first sound processing program to operating in accordance with a second sound processing program, etc.). Put another way, impedance response facility 1204 may implement parameter adjustment facility 304, thereby rendering apparatus 1200 into an implementation of apparatus 300.

As another example of an impedance response operation, impedance response facility 1204 may direct (e.g., based on the impedance of the electrode determined by impedance determination facility 1202) the cochlear implant system to measure an additional parameter associated with at least one of the patient and the cochlear implant system.

As yet another example of an impedance response operation, impedance response facility 1204 may determine (e.g., based on the determination of the impedance of the electrode by impedance determination facility 1202) an amount by which the impedance of the electrode has changed as compared to a baseline impedance of the electrode. If the amount by which the impedance of the electrode has changed is greater than a predetermined threshold (e.g., and only when the amount is greater than the predetermined threshold), impedance response facility 1204 may generate and store a record representative of the impedance of the electrode.

In like manner, as yet another example of an impedance response operation, impedance response facility 1204 may generate and store (e.g., based on the determination of the impedance of the electrode by impedance determination facility 1202) a record representative of the impedance of the electrode. Based on the record representative of the impedance of the electrode and further based on a plurality of other stored records representative of other impedances of the electrode or other electrodes, impedance response facility 1204 may determine a relative status of the impedance of the electrode with respect to the other impedances. In response to determining this relative status, impedance response facility 1204 may generate data representative of the relative status and adapted for presentation to a user associated with the cochlear implant system.

Any of these or other impedance response operations may be performed by any implementation of apparatus 1200. These impedance response operations and other impedance response operations related to them will be described in more detail below.

Storage facility 1206 may maintain any suitable data received, generated, managed, maintained, used, and/or transmitted by facilities 1202 or 1204 in a particular implementation. For example, as shown, storage facility 1206 may include impedance data 1208, which may include data associated with determining electrode impedances such as stimulation levels (e.g., patient specific stimulation levels), predetermined current levels (e.g., impedance test current levels) that are to be applied to the patient, electrode voltage levels, electrode impedance levels, and/or any other data as may facilitate facilities 1202 and 1204 in performing the operations described herein. Similarly, storage facility 1206 may include response data 1210, which may include data associated with performing one or more of the response operations described herein. Storage facility 1206 may maintain additional or alternative data as may serve a particular implementation.

The focus of the apparatuses and methods described herein may relate primarily to the types of operations performed by facilities 1202, 1204, and 1206 described above. However, it will be understood that, in various implementations, apparatus 1200 may include additional facilities to perform additional operations not explicitly described herein, or that are outside the scope of the present disclosure. For example, if apparatus 1200 is implemented as a mobile computing device (e.g., a smartphone), various facilities may be used to perform operations such as executing other applications, communicating with a provider network to provide voice, text, and other communications for a user, and the like. As another example, if apparatus 1200 is implemented as a sound processor or an integrated cochlear implant within a cochlear implant system, various additional facilities may be used to perform stimulation management operations with respect to an audio signal presented to a cochlear implant patient (e.g., an audio signal detected by a microphone). For instance, apparatus 1200 may receive an audio signal presented to the patient and perform one or more pre-processing operations, spectral analysis operations, noise reduction operations, mapping operations, and/or any other types of signal processing operations with respect to the received audio signal as may serve a particular application.

Additional details related to various impedance response operations (e.g., impedance response operations other than those related to setting cochlear implant system stimulation parameters as have been described in detail above) will now be described.

As one example of an impedance response operation that may be performed after apparatus 1200 determines the electrode impedance of an electrode, apparatus 1200 may direct the cochlear implant system to measure an additional parameter associated with at least one of the patient and the cochlear implant system. For example, apparatus 1200 may direct the cochlear implant system to measure the additional parameter based on the determined impedance of the electrode. As described above, apparatus 1200 may be implemented by a cochlear implant within the cochlear implant system (e.g., cochlear implant system 100 as illustrated in FIG. 12 or another cochlear implant system such as cochlear implant system 500 in other implementations), by a sound processor within the cochlear implant system, by a mobile computing device used by a user associated with the cochlear implant and separate from (but communicatively coupled with) the sound processor and the cochlear implant (e.g., mobile computing device 402), or by another suitable apparatus as may serve a particular application.

The additional parameter associated with at least one of the patient and the cochlear implant system that apparatus 1200 directs the cochlear implant system to measure may be any suitable parameter as may serve a particular implementation. As such, the measurement of the additional parameter may be used to implement any data logging, system checks, safety measures, or other functionality that may serve a particular implementation.

For instance, apparatus 1200 may direct the cochlear implant system to measure the additional parameter by directing the cochlear implant system to apply a test stimulus (e.g., a predetermined amount of stimulation current, a sound or other acoustic stimulation, etc.) to the patient and by measuring an evoked response that occurs in response to the application of the test stimulus. For example, if the test stimulus includes acoustic stimulation (e.g., for a patient with at least some residual hearing), the additional parameter measured by the cochlear implant system (i.e., the evoked response that occurs in response to the application of the acoustic stimulation applied to the patient) may include an electrocochleographic ("ECoG") evoked potential, an acoustic brainstem response, a compound action potential, or the like. Additionally or alternatively, if the test stimulus includes electrical stimulation (e.g., delivered by way of one or more electrodes implanted within the cochlea of the patient), the additional parameter measured by the cochlear implant system may include an electrically elicited compound action potential, or another suitable electrically elicited potential.

In the same or other examples, the additional parameter measured by the cochlear implant system may include an electrode impedance, evoked response, or other such measurement performed with respect to another electrode (e.g., a different electrode from that which the initial electrode impedance is measured). For instance, the additional parameter may be an electrode impedance of an electrode used by a contralateral cochlear implant within the cochlear implant system (e.g., an electrode associated with a cochlear implant associated with the opposite ear as the cochlear implant for which the initial electrode impedance is measured). Specifically, apparatus 1200 may direct the cochlear implant system to measure the additional parameter by directing the contralateral cochlear implant to generate additional electrical stimulation current at an additional predetermined current level and to apply the additional electrical stimulation current to the patient by way of an additional electrode coupled with the contralateral cochlear implant. Subsequently, apparatus 1200 may direct the contralateral cochlear implant to measure an additional voltage level associated with the additional electrode while the additional electrical stimulation current is applied to the patient by way of the additional electrode, and may determine an impedance of the additional electrode based on the additional predetermined current level and the measured additional voltage level. As such, the additional parameter measured by the cochlear implant system may be the impedance of the additional electrode coupled with the contralateral cochlear implant.

Based on the measurement of the additional parameter (e.g., the evoked response that occurs in response to the application of the test stimulus, the contralateral electrode impedance or evoked response measurement, etc.), apparatus 1200 may make any additional determination or perform any additional operation as may serve a particular implementation. For instance, as a first example, a change in electrode impedance for a patient who retains some residual hearing ability may, in certain circumstances, indicate that a condition of the patient (e.g., a sickness, an infection, etc.) is associated with risk to additional hearing loss for the patient. As such, apparatus 1200 may determine, based on a measurement of an evoked response, that a residual hearing ability of the patient is threatened by a current condition of the patient, and, in response to the determination that the residual hearing ability of the patient is threatened by the current condition of the patient, may generate an alert indicative of the threat to the residual hearing ability and adapted for presentation to a user associated with the cochlear implant system. In this way, the user (e.g., the patient, a caretaker of the patient, a clinician associated with the patient, etc.) may take appropriate measures to ensure that the patient timely receives necessary medical attention to avoid further loss of his or her residual hearing ability. For example, the user may timely request, obtain, and/or use medications (e.g., steroids, etc.) to mitigate the risks that have been detected.

As another example, a localized change in electrode impedance (i.e., a change that is not reflected contralaterally to electrodes implanted within both cochleae of the patient) may be associated with (e.g., likely to be caused by) one or more particular risks such as that a Meniere's episode may be impending. As such, apparatus 1200 may determine (e.g., based on the measurements of both the impedance of the initial electrode and the impedance of the additional electrode coupled with the contralateral cochlear implant) that the electrode impedance of the initial electrode is affected by a localized impedance change. In other words, apparatus 1200 may determine that the additional electrode coupled with the contralateral cochlear implant does not exhibit an electrode impedance change similar to that detected for the initial electrode coupled with the cochlear implant. Accordingly, based on the determination that the impedance of the electrode is affected by the localized impedance change, apparatus 1200 may determine that the patient is likely to experience a Meniere's episode, and, in response to the determination that the patient is likely to experience the Meniere's episode, may generate an alert indicative of the likelihood of the patient to experience the Meniere's episode (e.g., an alert similar to the one illustrated in FIG. 10B). As with other alerts described herein, the alert may be adapted for presentation to any user associated with the cochlear implant system as may serve a particular implementation (e.g., the patient himself or herself, a caretaker of the patient, a clinician or other medical personnel associated with the patient, etc.).

In other examples, in addition or as an alternative to determining that the patient is likely to experience the Meniere's episode, apparatus 1200 may determine (e.g., based on the determination that the impedance of the electrode is affected by the localized impedance change) that the patient is likely to experience a middle ear effusion episode. As such, apparatus 1200 may generate (e.g., in response to the determination that the patient is likely to experience the middle ear effusion episode) an alert indicative of the likelihood of the patient to experience the middle ear effusion episode (e.g., an alert similar to the one illustrated in FIG. 10A). Again, the alert may be adapted for presentation to any suitable user associated with the cochlear implant system in any suitable way.

As yet another example, a systemic change in electrode impedance (i.e., a non-localized change that is reflected contralaterally to electrodes implanted within both cochleae of the patient) may be associated with (e.g., likely to be caused by) one or more particular risks such as that a common cold or other sickness may be impending for the patient. As such, apparatus 1200 may determine (e.g., based on the measurements of both the impedance of the initial electrode and the impedance of the additional electrode coupled with the contralateral cochlear implant) that the impedance of the electrode is affected by a systemic impedance change. In other words, apparatus 1200 may determine that the additional electrode coupled with the contralateral cochlear implant exhibits an electrode impedance change similar to that detected for the initial electrode coupled with the cochlear implant. Accordingly, based on the determination that the impedance of the electrode is affected by the systemic impedance change, apparatus 1200 may determine that the patient is likely to experience a common cold episode, and, in response to the determination that the patient is likely to experience the common cold episode, may generate an alert indicative of the likelihood of the patient to experience of the common cold episode. The alert may be adapted for presentation to a user associated with the cochlear implant system as with other alerts described herein.

As another example of an impedance response operation that may be performed after apparatus 1200 determines (e.g., based on a predetermined current level and a measured voltage level) the electrode impedance of an electrode, apparatus 1200 may determine an amount by which the impedance of the electrode has changed as compared to a baseline impedance of the electrode, and, only when the amount by which the impedance of the electrode has changed is greater than a predetermined threshold, may generate and store a record representative of the impedance of the electrode. For example, apparatus 1200 may determine the amount by which the impedance of the electrode has changed and generate and store the record based on the determined impedance of the electrode. As described above, apparatus 1200 may be implemented by a cochlear implant within the cochlear implant system, by a sound processor within the cochlear implant system, by a mobile computing device used by a user associated with the cochlear implant and separate from (but communicatively coupled with) the sound processor and the cochlear implant (e.g., mobile computing device 402), or by another suitable apparatus as may serve a particular application.

By determining the amount by which the electrode impedance has changed in comparison to a baseline impedance and generating and storing a record representative of the impedance of the electrode only when the amount is greater than a predetermined threshold, apparatus 1200 may provide various benefits. For example, by selectively logging electrode impedance measurements in this way (i.e., rather than logging all electrode impedance measurements including those that do not represent significant changes to the baseline impedance), apparatus 1200 may help conserve resources (e.g., storage resources, processing resources), make it easier for users (e.g., clinicians, patients who wish to monitor their electrode impedances, etc.) to monitor and detect important changes with respect to the cochlear implant system, and otherwise improve logging and system monitoring operations for users.

This may be particularly helpful in implementations where apparatus 1200 is configured to measure the electrode impedances of the cochlear implant system often (e.g., hourly, minute-by-minute, etc.) during normal use of the cochlear implant system. If apparatus 1200 logs (i.e., generates and stores) a record for every measurement made in these types of scenarios, the amount of data logged away may become relatively cumbersome and/or difficult to store, use, and analyze. For example, conventionally, electrode impedances may have only been measured once or twice a year when the patient visited the clinic, thereby generating significantly less electrode impedance measurement data for systems and personnel to store, analyze, and use than apparatus 1200 may generate in the examples described herein. As such, by selectively logging only those records that may be determined to be important and/or the records surrounding them (e.g., measurements taken shortly before or after the measurements selected for logging), apparatus 1200 may facilitate storage, analysis, human understanding, and/or use of the logged records.

The baseline impedance of the electrode to which the electrode impedance is compared (i.e., to determine the amount by which the electrode impedance has changed) may be determined in any suitable way. For example, apparatus 1200 may determine the baseline impedance by designating a previous electrode impedance measurement (e.g., the last electrode impedance measurement that was made) to be the baseline impedance. In other examples, apparatus 1200 may determine the baseline impedance by basing the baseline impedance on (e.g., designating the baseline impedance to be) a fitting impedance of the electrode measured during a fitting session of the cochlear implant system to the patient. For instance, the fitting impedance may be a previous electrode impedance measured by a clinician during the fitting session using equipment at the clinic.

In still other examples, apparatus 1200 may determine the baseline impedance by basing the baseline impedance on (e.g., designating the baseline impedance to be) a "compliance impedance" of the electrode. For instance, the compliance impedance may be associated with a maximum or a minimum impedance of the electrode at which the cochlear implant system will operate within a normal compliance mode (e.g., if the cochlear implant system applies stimulation to the patient by way of the electrode at the maximum or minimum impedance, respectively). Thus, for example, if it is determined that a particular electrode impedance, if reached, will cause the cochlear implant system to operate outside of the normal compliance mode, the baseline impedance may be designated to be the particular electrode impedance and the predetermined threshold may be set close enough to the particular electrode impedance to indicate that the cochlear implant system is likely to operate outside of the normal mode of compliance (e.g., allowing an alert to be sent to a user associated with the cochlear implant system or another suitable operation to be performed).

Similarly, in other examples, apparatus 1200 may determine the baseline impedance by basing the baseline impedance on (e.g., designating the baseline impedance to be) a "stimulation rate impedance" of the electrode. For instance, the stimulation rate impedance may be associated with a maximum or a minimum impedance of the electrode at which the cochlear implant system will apply the stimulation to the patient at no less than a predetermined minimum allowable stimulation rate (e.g., if the cochlear implant system applies stimulation to the patient by way of the electrode at the maximum or minimum impedance, respectively). Thus, for example, if it is determined that a particular electrode impedance, if reached, will cause the cochlear implant system to apply stimulation to the patient at a stimulation rate that is too low (e.g., that degrades sound quality due to applying stimulation to the electrode for too long of a period of time on each phase to suitably charge the other electrodes), the baseline impedance may be designated to be the particular electrode impedance and the predetermined threshold may be set close enough to the particular electrode impedance to indicate that the cochlear implant system is likely to operate at less than the predetermined minimum allowable stimulation rate (e.g., allowing an alert to be sent to a user associated with the cochlear implant system or another suitable operation to be performed).

In like manner, in yet other examples, apparatus 1200 may determine the baseline impedance by basing the baseline impedance on (e.g., designating the baseline impedance to be) a "battery life impedance" of the electrode. For instance, the battery life impedance may be associated with a maximum or a minimum impedance of the electrode at which the cochlear implant system will apply the stimulation to the patient so as to consume no more than a maximum amount of battery power required for a battery life of the cochlear implant system to meet a prespecified minimum battery life limit (e.g., if the cochlear implant system applies stimulation to the patient by way of the electrode at the maximum or minimum impedance, respectively). Thus, for example, if it is determined that a particular electrode impedance, if reached, will cause the cochlear implant system to consume battery life too rapidly (e.g., fast enough to not meet the prespecified minimum battery life limit specified for the cochlear implant system), the baseline impedance may be designated to be the particular electrode impedance and the predetermined threshold may be set close enough to the particular electrode impedance to indicate that the cochlear implant system is likely to consume more than the maximum amount of battery power required for the battery life to meet the prespecified minimum battery life limit (e.g., allowing an alert to be sent to a user associated with the cochlear implant system or another suitable operation to be performed).

In other examples, apparatus 1200 may determine the baseline impedance by basing the baseline impedance on (e.g., designating the baseline impedance to be) an "historical average impedance" of the electrode over a time period. For instance, the historical average impedance may be based on the determination of the impedance of the electrode and on one or more additional stored records representative of previous impedances of the electrode or other electrodes. Thus, for example, the historical average impedance may represent an average impedance for the electrode currently being measured, an average impedance for all the electrodes associated with a particular cochlear implant or with a particular patient, or an average impedance for all the electrodes associated with a particular clinician, clinic, or the like. Apparatus 1200 may base the baseline impedance on the historical average impedance of the electrode over the time period (e.g., by designating the baseline impedance to be the historical average, to be offset from the historical average by a set margin, etc.).

To be most useful as an electrode impedance log, apparatus 1200 may store, along with the record representative of the electrode impedance, any other suitable data as may serve a particular implementation. For example, apparatus 1200 may generate and store the record representative of the impedance of the electrode by detecting a time at which the voltage level is measured, and including (e.g., within the generated and stored record representative of the impedance of the electrode) data representative of the detected time at which the voltage level is measured to indicate a timestamp with which the determined impedance of the electrode is associated.

To further increase the usefulness of electrode impedance logs generated by the selective logging of electrode impedances described herein, apparatus 1200 may generate and store the record representative of the impedance of the electrode by identifying (e.g., based on one or more predetermined criteria) that the determined impedance of the electrode is of particular importance, and including (e.g., within the generated and stored record representative of the impedance of the electrode) data representative of a flag indicative of the particular importance that the determined impedance of the electrode represented within the record is identified to have. For example, the predetermined threshold may be set relatively permissively to broadly allow lots of electrode impedance records to be stored (e.g., as long as they represent at least a somewhat significant electrode impedance change). However, if a particular measurement is particularly significant (e.g., if the measurement exceeds a second, narrower predetermined threshold or the like), apparatus 1200 may flag the measurement in this way to ensure that the measurement is brought to the attention of the clinician, patient, and/or other user who may be reviewing and/or analyzing the data logs.

As yet another example of an impedance response operation that may be performed after apparatus 1200 determines (e.g., based on a predetermined current level and a measured voltage level) the electrode impedance of an electrode, apparatus 1200 may analyze and present electrode impedance data from electrode impedance logs. In other words, for instance, apparatus 1200 may generate and store (e.g., based on the determination of the impedance of the electrode) a record representative of the impedance of the electrode, determine (e.g., based on the record representative of the electrode impedance) a relative status of the electrode impedance, and generate (e.g., in response to the determination of the relative status of the impedance of the electrode) data representative of the relative status. For instance, in some examples, the relative status may be based on a plurality of other stored records representative of other electrode impedances (e.g., previous electrode impedances of the electrode, electrode impedances of other electrodes, etc.), and, as such, the relative status of the electrode impedance may be a relative status of the electrode impedance with respect to the other electrode impedances. Moreover, in the same or other examples, the data representative of the relative status may be adapted for presentation to a user associated with the cochlear implant system, such as a patient, caregiver, clinician, or other user described herein.

By logging (e.g., generating and storing) records representative of the electrode impedance, determining the relative status of the electrode impedance with respect to the other electrode impedances, and generating the data representative of the relative status, apparatus 1200 may provide various benefits. For instance, data analytics associated with these types of logged data may reveal an assortment of helpful, useful, or interesting statistics, including insights that may facilitate patients in improving their hearing (e.g., their use of the cochlear implant system), clinicians in improving their practices, organizations (e.g., hearing clinics, etc.) in improving their effectiveness or profitability, and so forth. Specifically, apparatus 1200 may reveal these helpful statistics and insights by determining and analyzing not only those measurements related to a present performance of a particular electrode, cochlear implant system, or patient, but also by determining (e.g., based on other measurements) how that present performance compares to that of past performances, or to the performances of other electrodes, cochlear implant systems, or patients.

To this end, the relative status may relate to any suitable status, characteristic, performance, standing, etc., of the electrode impedance with respect to other impedances. For example, apparatus 1200 may determine the relative status of the electrode impedance with respect to the other impedances by determining an average impedance of the electrode and/or the other electrodes over a time period (e.g., based on at least some of the plurality of other stored records representative of the other impedances), determining a variance associated with the average impedance, and determining (e.g., based on the average impedance and the variance associated with the average impedance) the relative status of the impedance of the electrode. More specifically, apparatus 1200 may determine the relative status based on how much the impedance of the electrode deviates from the average impedance with respect to the variance associated with the average impedance.

In certain examples, an average (e.g., mean, median, etc.) electrode impedance may be determined for all the electrode impedance measurements of the electrode or for the electrode impedance measurements of several electrodes (e.g., all the electrodes associated with a particular cochlear implant, all the electrodes associated with a particular cochlear implant system or patient, all the electrodes associated with patients of a particular clinician or a particular clinic, etc.). Subsequently, the variance of the average electrode impedance measurements (e.g., related to a standard deviation of the electrode impedance measurements) may be determined to give an indication of how much the electrode impedance measurements vary from the average. Based on the average electrode impedance and the variance associated with the average impedance, apparatus 1200 may determine that the impedance of the electrode deviates from the average impedance by at least a predetermined deviation with respect to the variance associated with the average impedance deviation. In other words, apparatus 1200 may objectively determine that a particular electrode impedance measurement (e.g., associated with a particular electrode, cochlear implant system, and patient, etc.), falls outside the norm or is at least somewhat out of the ordinary.

As a result (e.g., in response to the determination that the impedance of the electrode deviates from the average impedance by at least the predetermined deviation), apparatus 1200 may generate an alert indicating that the electrode deviates from the average impedance by at least the predetermined deviation with respect to the variance associated with the average impedance deviation. For example, the alert may be adapted for use by a user associated with the cochlear implant system such as a clinician, who may treat the electrode, cochlear implant system, and/or patient associated with the measurement differently based on the knowledge that the measurement is at least somewhat out of the ordinary. Conversely, if no alert is generated, the user (e.g., the clinician) may confidently treat the electrode, cochlear implant system, patient, etc., according to standard or established routines that are appropriate for electrodes, cochlear implant systems, patients, etc., that are not out of the ordinary.

The other records upon which the average impedance and the variance are based may include records from any suitable measurements associated with any suitable electrodes, cochlear implant systems, patients, or the like, as may serve a particular implementation. For example, at least some of the plurality of the other stored records upon which the average impedance is based may include stored records representative of previous impedances of the electrode measured for the patient during the time period. In one implementation, for instance, the average impedance may be based on all the measurements taken of the electrode over the past year, such that the average impedance may indicate that the electrode is on the high end or the low end of what it usually is, is exceptional (e.g., the highest or lowest it has been in the last year), is right near the average of what it has typically been during the last year, or the like.

As another example of what other stored records the average impedance and the variance may be based on, at least some of the plurality of the other stored records may include stored records representative of impedances of other electrodes associated with other patients who are all associated with a particular clinic during the time period, who are all associated with a particular medical professional (e.g., a particular clinician, a particular surgeon who implanted the cochlear implant, etc.) during the time period, who are all associated with a particular geographical region during the time period, or the like. For example, an electrode impedance measurement may seem to be exceptionally high or low by itself or in comparison to previous measurements until the measurement is compared to other measurements of patients who have similar circumstances (e.g., live in the same climate, go to the same clinician, etc.). Specifically, for instance, patients who visit a clinic located in Alaska, as a group, may tend to have significantly different electrode impedances and/or significantly wider or narrower variances than do patients who visit a clinic in Florida (e.g., due to significant climate differences, etc.).

The relative status indicating whether a particular measurement, electrode, cochlear implant system, patient, etc., is close to the norm or is exceptional may be presented using any suitable type of data or alert that is adapted for presentation to any suitable user associated with the cochlear implant system. For example, apparatus 1200 may generate the data representative of the relative status by generating at least one quantitative indicator of the relative status adapted for presentation to the user as at least one of a textual message and a graphical image. More specifically, for instance, the data may include one or more numbers (e.g., measured numbers, average numbers, variance-related numbers, percentile numbers, etc.) that are shown on a graph or described in a textual message.

Additionally or alternatively, apparatus 1200 may generate the data representative of the relative status by generating at least one qualitative indicator of the relative status adapted for presentation to the user as a graphical image representative of a subjective level selected from a plurality of subjective levels. More specifically, for example, the relative status may be indicated by a green, yellow, or red indicator (i.e., green for qualitatively "good," yellow for qualitatively "fair," red for qualitatively "needs improvement," or the like). Similarly, the relative status may be indicated by one of several levels or grades (e.g., from a grade of 'A' to an 'F', from a level '1' to a level '5', etc.), or any other qualitative indicators as may serve a particular implementation.

Moreover, as described above, in certain examples, an audio simulation may be used to present the data to help a user other than the patient understand what the patient is experiencing in terms of sound quality. For instance, if an electrode impedance measurement is relatively out of the ordinary (e.g., displaced relatively far from the impedance average in light of the variance of the impedance average), a user associated with the cochlear implant system other than the patient (e.g., a caretaker of the patient or the like) may select to hear an audio simulation of what the patient is experiencing while the electrode has the relative status (e.g., while the electrode impedance is at the current level). In response, apparatus 1200 may generate the data representative of the relative status by generating at least one audible indicator of the relative status adapted for presentation to the person as an audio simulation that, when listened to by the user (e.g., the caretaker), simulates a hearing experience provided to the patient by the cochlear implant system while the electrode has the relative status. For example, the audio simulation may include channel clipping, channel compression, reduced stimulation rates, and/or other factors to help parents, clinicians, and others better understand the sound quality (or lack thereof) experienced by the patient.

As described above, and as illustrated in, for example, FIG. 5, apparatus 1200 may be implemented by any of various devices inside or outside of a cochlear implant system. One specific type of apparatus that may implement apparatus 1200 that has been mentioned is a cochlear implant included within the cochlear implant system. For example, as shown in FIG. 5, such a cochlear implant may be an integrated cochlear implant (e.g., integrated cochlear implant 504) that includes a sound processor (e.g., sound processor 506). In other examples, such as illustrated in FIG. 1, such a cochlear implant may be a cochlear implant (e.g., cochlear implant 108) that communicates with an external sound processor (e.g., sound processor 104).

In any case, a cochlear implant included within a cochlear implant system used by a patient may include various components used to perform various operations described herein (e.g., operations performed by apparatus 1200). For example, the cochlear implant may include a current generation circuit that generates electrical stimulation current at a predetermined current level and applies the electrical stimulation current to the patient by way of an electrode coupled with the cochlear implant. The cochlear implant may further include a voltage detector that measures a voltage level associated with the electrode while the electrical stimulation current is applied to the patient by way of the electrode. Additionally, the cochlear implant may include at least one physical computing component (e.g., a processor, a memory storing executable instructions, digital logic, etc.) that directs the current generation circuit to generate and apply the electrical stimulation current at the predetermined current level, directs the voltage detector to measure the voltage level while the electrical stimulation current is applied to the patient, determines (e.g., based on the predetermined current level and the measured voltage level) an impedance of the electrode, and generates a record representative of the determined impedance of the electrode.

This cochlear implant may perform any of the operations (e.g., impedance response operations) described herein (e.g., in relation to apparatus 1200 and/or other systems and methods described herein). For instance, the cochlear implant may direct a sound processor included within the cochlear implant system to store the generated record representative of the determined impedance of the electrode. Based on the direction from the cochlear implant, the sound processor may store the generated record representative of the determined impedance of the electrode within a backup device associated with the sound processor. For example, the backup device may include (e.g., be implemented by) an onboard local storage facility included within the sound processor or a remote storage facility included within a device communicatively coupled with the sound processor (e.g., a smart battery that includes storage space and powers the sound processor, a mobile computing device communicatively coupled with the sound processor such as mobile computing device 402 in FIGS. 4 and 5, or the like). As such, additionally or alternatively, the cochlear implant may further direct a mobile computing device separate from and communicatively coupled with the cochlear implant to store the generated record representative of the determined impedance of the electrode.

Moreover, in certain implementations, the cochlear implant may determine (e.g., based on the determined impedance of the electrode) that the cochlear implant system is operating outside of a normal compliance mode. In response to the determination that the cochlear implant system is operating outside of the normal compliance mode, the cochlear implant may generate an alert associated with the impedance of the electrode and adapted for presentation to a user associated with the cochlear implant system. For example, as described above, the alert may indicate that the cochlear implant system is operating outside of the normal compliance mode and may be adapted for presentation to any suitable type of user (e.g., the patient, a caregiver, a clinician, etc.).

Additionally, the cochlear implant may direct (e.g., based on the determined impedance of the electrode) the sound processor included within the cochlear implant system to automatically adjust a stimulation parameter associated with the cochlear implant system. Moreover, as described above in relation to apparatus 300, the cochlear implant may further identify an adjustment constraint and the sound processor may automatically adjust the stimulation parameter in accordance with the adjustment constraint. For example, the stimulation parameter being automatically adjusted in accordance with the adjustment constraint may be a pulse width associated with stimulation pulses applied to the patient by way of the electrode during normal operation of the cochlear implant system.

In certain examples, as further described above in relation to apparatus 300, the cochlear implant may direct (e.g., based on the determined impedance of the electrode) a sound processor included within the cochlear implant system to switch from operating in accordance with a first sound processing program to operating in accordance with a second sound processing program. Similarly, as with apparatus 300 described above, the cochlear implant may generate (e.g., in response to the determination of the impedance of the electrode) an alert associated with the impedance of the electrode and adapted for presentation to a user associated with the cochlear implant system.

In some examples, the cochlear implant may temporarily disable, based on the determined impedance of the electrode, the electrode such that the electrode abstains from applying stimulation pulses to the patient for a period of time during normal operation of the cochlear implant system.

Additionally or alternatively, in certain implementations, the cochlear implant may determine (e.g., based on the determination of the impedance of the electrode) an amount by which the impedance of the electrode has changed as compared to a baseline impedance of the electrode, and determine that the amount by which the impedance of the electrode has changed is greater than a predetermined threshold. As such, the cochlear implant may generate the record representative of the determined impedance of the electrode in response to the determination that the amount by which the impedance of the electrode has changed is greater than the predetermined threshold.

As described above in relation to apparatus 1200, the baseline impedance of the electrode to which the impedance of the electrode is compared to determine the amount by which the impedance of the electrode has changed may be based on a fitting impedance of the electrode measured during a fitting session of the cochlear implant system to the patient. Additionally or alternatively, the baseline impedance of the electrode to which the impedance of the electrode is compared may be based on a compliance impedance, a stimulation rate impedance, a battery life impedance, or another suitable impedance associated with the electrode, as described above.

The cochlear implant may generate the record representative of the determined impedance of the electrode in any manner (and including any supplemental data) as may serve a particular implementation. For example, the cochlear implant may generate the record by detecting a time at which the voltage level is measured, and including (e.g., within the generated record representative of the determined impedance of the electrode) data representative of the detected time at which the voltage level is measured to indicate a timestamp with which the determined impedance of the electrode is associated.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An apparatus associated with a cochlear implant system used by a patient, the apparatus comprising:
    at least one physical computing component that
        directs a cochlear implant included within the cochlear implant system and implanted within the patient to generate electrical stimulation current at a predetermined current level and to apply the electrical stimulation current to the patient by way of an electrode coupled with the cochlear implant;
        directs the cochlear implant to measure a voltage level associated with the electrode while the electrical stimulation current is applied to the patient by way of the electrode;
        determines, based on the predetermined current level and the measured voltage level, an impedance of the electrode;
        identifies a tentative stimulation parameter adjustment constraint and an absolute stimulation parameter adjustment constraint for a stimulation parameter associated with the cochlear implant system;
automatically adjusts, based on the impedance of the electrode and in accordance with the tentative stimulation parameter adjustment constraint, the stimulation parameter within a range between a present value and a first value defined by the tentative stimulation parameter adjustment constraint; and
further adjusts, based on user input provided by the patient to the cochlear implant system and in accordance with the absolute stimulation parameter adjustment constraint, the stimulation parameter within a range between the first value and a second value that is defined by the absolute stimulation parameter adjustment constraint and is beyond the first value defined by the tentative stimulation parameter adjustment constraint.

2. The apparatus of claim 1, wherein:
the tentative and absolute stimulation parameter adjustment constraints are determined and set within a storage component included within the apparatus by a medical professional facilitating care of the patient with respect to the cochlear implant system; and
the at least one physical computing component identifies the tentative and absolute stimulation parameter adjustment constraints by retrieving the tentative and absolute stimulation parameter adjustment constraints from the storage component.

3. The apparatus of claim 2, wherein:
the stimulation parameter is a pulse width associated with stimulation pulses applied to the patient by way of the electrode during a normal operation of the cochlear implant system;
the tentative stimulation parameter adjustment constraint determined and set by the medical professional defines a tentative maximum pulse width;
the absolute stimulation parameter adjustment constraint determined and set by the medical professional defines an absolute maximum pulse width;
the at least one physical computing component automatically adjusts the stimulation parameter by automatically increasing the pulse width associated with the stimulation pulses to a pulse width longer than a present pulse width and below the tentative maximum pulse width; and
the at least one physical computing component further adjusts the stimulation parameter by increasing the pulse width associated with the stimulation pulses to a pulse width longer than the tentative maximum pulse width and below the absolute maximum pulse width.

4. The apparatus of claim 2, wherein:
the stimulation parameter is a target stimulation voltage associated with stimulation pulses applied to the patient by way of the electrode during a normal operation of the cochlear implant system;
the tentative stimulation parameter adjustment constraint determined and set by the medical professional defines a tentative maximum target stimulation voltage;
the absolute stimulation parameter adjustment constraint determined and set by the medical professional defines an absolute maximum target stimulation voltage;
the at least one physical computing component automatically adjusts the stimulation parameter by automatically increasing the target stimulation voltage associated with the stimulation pulses to a target stimulation voltage larger than a present target stimulation voltage and below the tentative maximum target stimulation voltage; and
the at least one physical computing component further adjusts the stimulation parameter by increasing the target stimulation voltage associated with the stimulation pulses to a target stimulation voltage larger than the tentative target stimulation voltage and below the absolute maximum target stimulation voltage.

5. The apparatus of claim 2, wherein:
the stimulation parameter is a number of active electrodes applying stimulation pulses to the patient during a normal operation of the cochlear implant system;
the tentative stimulation parameter adjustment constraint determined and set by the medical professional defines a tentative minimum number of active electrodes;
the absolute stimulation parameter adjustment constraint determined and set by the medical professional defines an absolute minimum number of active electrodes;
the at least one physical computing component automatically adjusts the stimulation parameter by automatically decreasing the number of active electrodes applying the stimulation pulses to the patient to a number of active electrodes smaller than a present number of active electrodes and above the tentative minimum number of active electrodes; and
the at least one physical computing component further adjusts the stimulation parameter by decreasing the number of active electrodes applying the stimulation pulses to the patient to a number of active electrodes smaller than the tentative minimum number of active electrodes and above the absolute minimum number of active electrodes.

6. The apparatus of claim 1, wherein:
the at least one physical computing component further:
provides an alert associated with adjusting the stimulation parameter beyond the first value defined by the tentative stimulation parameter adjustment constraint,
receives the user input in response to the alert associated with adjusting the stimulation parameter beyond the first value defined by the tentative stimulation parameter adjustment constraint.

7. The apparatus of claim 1, wherein:
the tentative stimulation parameter adjustment constraint is associated with a predetermined adjustment timeline set by at least one of the patient, a caretaker of the patient, and a medical professional facilitating care of the patient with respect to the cochlear implant system; and
the predetermined adjustment timeline specifies
a plurality of automatic stepwise adjustments associated with the stimulation parameter to facilitate a gradual adjustment of the stimulation parameter from an initial value to a target value, and
designated time intervals to be inserted between the automatic stepwise adjustments in the plurality of automatic stepwise adjustments associated with the stimulation parameter.

8. The apparatus of claim 1, wherein, in accordance with the tentative stimulation parameter adjustment constraint, the at least one physical computing component automatically adjusts the stimulation parameter only during a powering-up sequence of the cochlear implant system.

9. The apparatus of claim 1, wherein the at least one physical computing component automatically adjusts the stimulation parameter by automatically directing a sound processor included within the cochlear implant system to switch from operating in accordance with a first sound processing program to operating in accordance with a second sound processing program.

10. The apparatus of claim 1, wherein the at least one physical computing component further:
   determines, based on the determined impedance of the electrode, that the cochlear implant system is operating outside of a normal compliance mode; and
   generates, in response to the determination that the cochlear implant system is operating outside of the normal compliance mode, an alert indicating that the cochlear implant system is operating outside of the normal compliance mode, the alert adapted for presentation to a user associated with the cochlear implant system.

11. The apparatus of claim 1, wherein the at least one physical computing component further:
   determines, based on the determined impedance of the electrode, that the patient is likely to experience a Meniere's episode; and
   generates, in response to the determination that the patient is likely to experience a Meniere's episode, an alert indicating that the patient is likely to experience the Meniere's episode, alert adapted for presentation to the patient.

12. The apparatus of claim 1, wherein the apparatus that is associated with the cochlear implant system and that comprises the at least one physical computing component is implemented by a sound processor included within the cochlear implant system.

13. The apparatus of claim 1, wherein the apparatus that is associated with the cochlear implant system and that comprises the at least one physical computing component is implemented by a mobile computing device that is separate from and communicatively coupled with the cochlear implant system.

14. A cochlear implant implanted within a patient and included within a cochlear implant system, the cochlear implant comprising:
   a stimulation current generator configured to generate electrical stimulation current to be applied to the patient by way of an electrode on an electrode lead coupled to the cochlear implant;
   a voltage detector configured to measure a voltage level associated with the electrode; and
   at least one physical computing component that
      directs the stimulation current generator to generate electrical stimulation current at a predetermined current level and to apply the electrical stimulation current to the patient by way of the electrode;
      directs the voltage detector to measure the voltage level associated with the electrode while the electrical stimulation current is applied to the patient by way of the electrode;
      determines, based on the predetermined current level and the measured voltage level, an impedance of the electrode;
      identifies a tentative stimulation parameter adjustment constraint and an absolute stimulation parameter adjustment constraint for a stimulation parameter associated with the cochlear implant system;
      automatically adjusts, based on the impedance of the electrode and in accordance with the tentative stimulation parameter adjustment constraint, the stimulation parameter within a range between a present value and a first value defined by the tentative stimulation parameter adjustment constraint; and
      further adjusts, based on user input provided by the patient to the cochlear implant system and in accordance with the absolute stimulation parameter adjustment constraint, the stimulation parameter within a range between the first value and a second value that is defined by the absolute stimulation parameter adjustment constraint and is beyond the first value defined by the tentative stimulation parameter adjustment constraint.

15. The cochlear implant of claim 14, wherein:
the tentative and absolute stimulation parameter adjustment constraints are determined and set within a storage component included within the cochlear implant system by a medical professional facilitating care of the patient with respect to the cochlear implant system; and
the at least one physical computing component identifies the tentative and absolute stimulation parameter adjustment constraints by retrieving the predetermined tentative and absolute stimulation parameter adjustment constraints from the storage component.

16. The cochlear implant of claim 15, wherein:
the stimulation parameter is a pulse width associated with stimulation pulses applied to the patient by way of the electrode during a normal operation of the cochlear implant system;
the tentative stimulation parameter adjustment constraint determined and set by the medical professional defines a tentative maximum pulse width;
the absolute stimulation parameter adjustment constraint determined and set by the medical professional defines an absolute maximum pulse width;
the at least one physical computing component automatically adjusts the stimulation parameter by automatically increasing the pulse width associated with the stimulation pulses to a pulse width longer than a present pulse width and below the tentative maximum pulse width; and
the at least one physical computing component further adjusts the stimulation parameter by increasing the pulse width associated with the stimulation pulses to a pulse width longer than the tentative maximum pulse width and below the absolute maximum pulse width.

17. The cochlear implant of claim 15, wherein:
the stimulation parameter is a target stimulation voltage associated with stimulation pulses applied to the patient by way of the electrode during a normal operation of the cochlear implant system;
the tentative stimulation parameter adjustment constraint determined and set by the medical professional defines a tentative maximum target stimulation voltage;
the absolute stimulation parameter adjustment constraint determined and set by the medical professional defines an absolute maximum target stimulation voltage;
the at least one physical computing component automatically adjusts the stimulation parameter by automatically increasing the target stimulation voltage associated with the stimulation pulses to a target stimulation voltage larger than a present target stimulation voltage and below the tentative maximum target stimulation voltage; and
the at least one physical computing component further adjusts the stimulation parameter by increasing the target stimulation voltage associated with the stimulation pulses to a target stimulation voltage larger than the tentative target stimulation voltage and below the absolute maximum target stimulation voltage.

18. The cochlear implant of claim 15, wherein:
the stimulation parameter is a number of active electrodes applying stimulation pulses to the patient during a normal operation of the cochlear implant system;
the tentative stimulation parameter adjustment constraint determined and set by the medical professional defines a tentative minimum number of active electrodes;
the absolute stimulation parameter adjustment constraint determined and set by the medical professional defines an absolute minimum number of active electrodes;
the at least one physical computing component automatically adjusts the stimulation parameter by automatically decreasing the number of active electrodes applying the stimulation pulses to the patient to a number of active electrodes smaller than a present number of active electrodes and above the tentative minimum number of active electrodes; and
the at least one physical computing component further adjusts the stimulation parameter by decreasing the number of active electrodes applying the stimulation pulses to the patient to a number of active electrodes smaller than the tentative minimum number of active electrodes and above the absolute minimum number of active electrodes.

19. The cochlear implant of claim 14, wherein:
the at least one physical computing component further:
provides an alert associated with adjusting the stimulation parameter to a value beyond the first value defined by the tentative stimulation parameter adjustment constraint,
receives the user input in response to the alert associated with adjusting the stimulation parameter beyond the first value defined by the tentative stimulation parameter adjustment constraint.

20. A method comprising:
directing, by an apparatus associated with a cochlear implant system used by a patient, a cochlear implant included within the cochlear implant system and implanted within the patient to generate electrical stimulation current at a predetermined current level and to apply the electrical stimulation current to the patient by way of an electrode coupled with the cochlear implant;
directing, by the apparatus, the cochlear implant to measure a voltage level associated with the electrode while the electrical stimulation current is applied to the patient by way of the electrode;
determining, by the apparatus based on the predetermined current level and the measured voltage level, an impedance of the electrode;
identifying, by the apparatus, a tentative stimulation parameter adjustment constraint and an absolute stimulation parameter adjustment constraint for a stimulation parameter associated with the cochlear implant system;
automatically adjusting, by the apparatus based on the impedance of the electrode and in accordance with the tentative stimulation parameter adjustment constraint, the stimulation parameter within a range between a present value and a first value defined by the tentative stimulation parameter adjustment constraint; and
further adjusting, by the apparatus based on user input provided by the patient to the cochlear implant system and in accordance with the absolute stimulation parameter adjustment constraint, the stimulation parameter within a range between the first value and a second value that is defined by the absolute stimulation parameter adjustment constraint and is beyond the first value defined by the tentative stimulation parameter adjustment constraint.

* * * * *